(12) United States Patent
Clark et al.

(10) Patent No.: US 6,268,215 B1
(45) Date of Patent: Jul. 31, 2001

(54) RECOMBINANT KERATINOCYTES

(75) Inventors: Richard A. Clark, Poquott, NY (US); Miyoko Kubo, Tamano (JP)

(73) Assignee: The Research Foundation of State University of New York, Albany, NY (US)

( * ) Notice: Subject to any disclaimer, the term of this patent is extended or adjusted under 35 U.S.C. 154(b) by 0 days.

(21) Appl. No.: 09/290,223

(22) Filed: Apr. 13, 1999

Related U.S. Application Data
(60) Provisional application No. 60/106,951, filed on Nov. 4, 1998.

(51) Int. Cl.$^7$ .................................................. C12N 5/16
(52) U.S. Cl. ................ 435/325.1; 536/23.5; 435/320.1; 435/455
(58) Field of Search ............................. 435/320.1, 69.1, 435/325, 371, 455; 424/93.1, 93.2, 93.21; 514/44; 536/23.5

(56) References Cited

FOREIGN PATENT DOCUMENTS
0846702A2 * 6/1998 (EP) ............................. C07K/14/705

OTHER PUBLICATIONS

Garlick et al. Crit Rev Oral Biol Med. 7(3): 204–221, 1996.*
Horch et al. Cell Transplantation. 7(3): 309–317, May 1998.*
Ledley, F.D. Pharmaceutical Research 13: 1595–1613, Nov. 1996.*
Choate et al. Human Gene Therapy. 8(14): 1659–65, Sep. 1997.*
Hultman et al. Journal of Trauma Injury. 45(1): 25–34, Jul. 1998.*
Rennekampf et al. J. Surgical Research. 62(2): 288–295, May 1996.*
Vogt et al. Proc. Natl Acad. Sci USA. 91: 9307–9311, Sep. 1994.*
Kubo et al. Journal of Investigative Dermatology. 106(4): 829, Apr. 1996.*
Kubo et al. Journal of Dermatological Science. 16, Suppl 1: S69, Mar. 1998.*
Phillips, T.J., et al., Journal of the American Academy of Dermatology 189–198 (1989).
Clark, R.A.F., et al., British Journal of Dermatology 135:46–51 (1996).
Wu, C., et al., Journal of Cell Science 108:821–829 (1995).
Kim, J.P., et al., Journal of Cellular Physiology 151:443–450 (1992).
Galileo, D.S., et al., Neuron (9):1117–1131 (1992).
Larjava, H., et al., Journal of Cellular Physiology 157:190–200 (1993).
Larjava, H., et al., J Clin Invest (92):1425–1435 (1993).
Alemany, M., et al., The American Society of Hematology 592–601 (1996).
Kim, J.P., et al., Laboratory Investigation 71(3):401–408 (1994).
Juhasz, I., et al., American Journal of Pathology 143(5):1458–1469 (1993).
Leavesley, D.I., et al., The Journal of Cell Biology 117(5):1101–1107 (1992).
Morgenstern, J.P., et al., Nucleic Acids Research 18(12):3587–3596 (1990).
Greenberg, Z., et al. Anal Biochem 266(1):153–164 (1999) Abstract Only.
Hsu, MY, et al., Am J Pathol 153(5):1435–1442 (1998) Abstract Only.
Seftor, RE., Am J Pathol 153(5):1347–1351 (1998) Title Only.
Faccio, R., et al., Biochem Biophys Res Commun 249(2):522–525 (1998) Abstract Only.
Yee, KO., et al., Circ Res 83(3):241–251 (1998) Abstract only.
Vailhe, B., et al., In Vitro Cell Dev Biol Anim 33(10):763–773 (1997) Abstract Only.
Simon, KO., et al., J Biol Chem 272(46):29380–29389 (1997) Abstract Only.
Horton, M.A., Int J Bochem Cell Biol 29(5):721–725 (1997) Abstract Only.
Asakura, S., J Biol Chem 272(13):8824–8829 (1997) Abstract Only.
Gerber, D.J., et al., Proc Natl Acad Sci USA 93(25):14698–14703 (1996) Abstract Only.
Danen, EH., et al., Biochem Biophys Res Commun 226(1):75–81 (1996) Abstract Only.
Marcinkiewicz, C., et al., Protein Expr Purif 8(1):68–74 (1996) Abstract Only.
Varner, JA., et al., Cell Adhes Commun 3(4):367–374 (1995) Title Only.
Lindberg, FP., et al., J Cell Biol 123(2):485–496 (1993) Abstract Only.
Leavesley, DI., et al., J Cell Biol 117(5):1101–1107 (1992) Abstract Only.
Cheresh, DA., Cancer Metastasis Rev 10(1):3–10 (1991) Abstract Only.
Cheresh, DA., Clin Lab Med 12(2):217–236 (1992) Abstract Only.

(List continued on next page.)

*Primary Examiner*—Deborah J. R. Clark
*Assistant Examiner*—Christopher E Drabik
(74) *Attorney, Agent, or Firm*—Braman & Rogalskyj, LLP

(57) ABSTRACT

The invention provides a recombinant keratinocyte having nucleic acid encoding a human β3 integrin subunit introduced therein. This recombinant keratinocyte is able to adhere to fibrin/fibrinogen, and therefore when used in a graft procedure the recombinant keratinocyte is able to adhere to fibrin/fibrinogen present in any fibrin clot in the wound. The invention thus further provides a method of enhancing wound healing in a graft procedure by using the recombinant keratinocytes.

1 Claim, 15 Drawing Sheets

OTHER PUBLICATIONS

Gladson, CL., et al., J Clin Invest 88(6):1924–1932 (1991) Abstract Only.

Charo, IF., et al., J Cell Biol 111(6 Pt 1):2795–2800 (1990) Abstract Only.

Smith, JW., et al., J Biol Chem 265(21):12267–12271 (1990) Abstract Only.

Smith, JW., et al., J Biol Chem 265(4):2168–2172 (1990) Abstract Only.

Cheresh, DA., et al., Cell 58(5):945–953 (1989) Abstract Only.

Cheresh, DA., et al., Cell 57(1):59–69 (1989) Abstract Only.

Felding–Habermann B., et al., Curr Opin Cell Biol 5(5):864–868 (1993) Abstract Only.

Weiss, E., et al., Journal of Cellular Physiology 174:58–65 (1998).

* cited by examiner

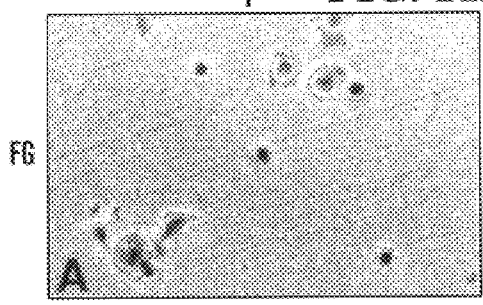
β3 *FIG. 11A* — FG
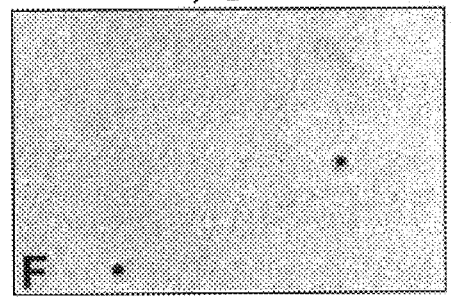
β-gal *FIG. 11F* — FG
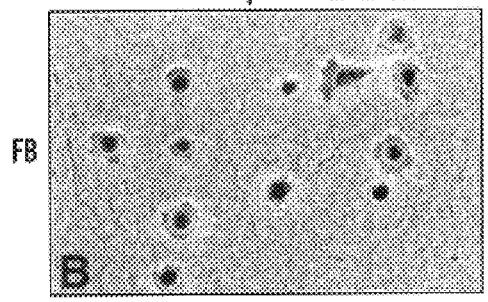
β3 *FIG. 11B* — FB
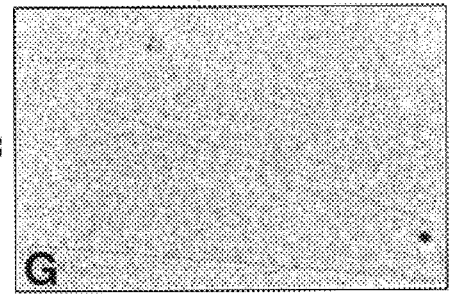
β-gal *FIG. 11G* — FB
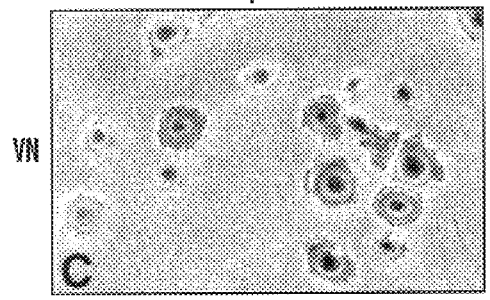
β3 *FIG. 11C* — VN
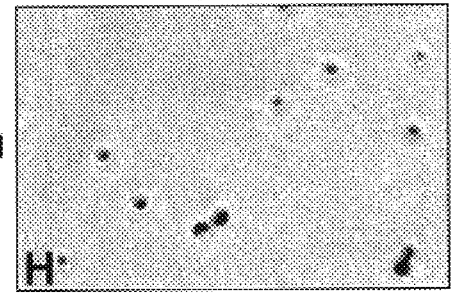
β-gal *FIG. 11H* — VN
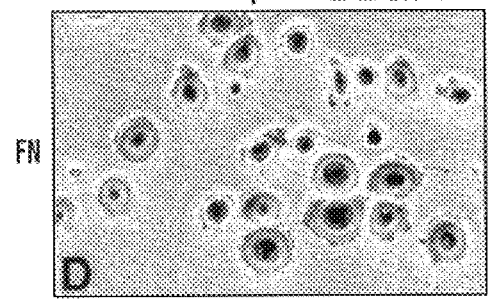
β3 *FIG. 11D* — FN
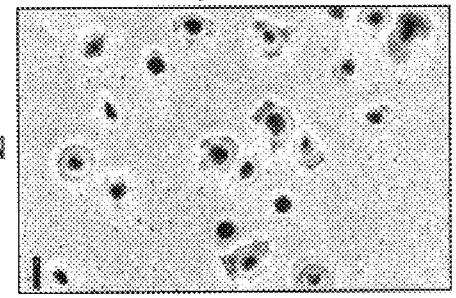
β-gal *FIG. 11I* — FN
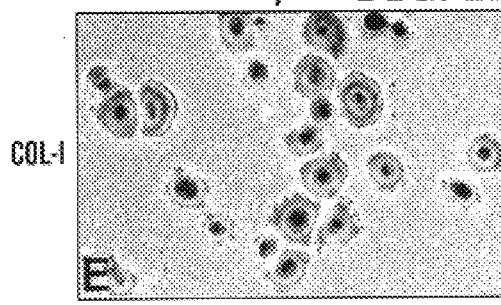
β3 *FIG. 11E* — COL-I
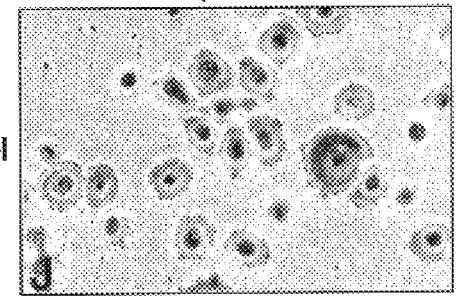
β-gal *FIG. 11J* — COL-I

RECOMBINANT KERATINOCYTES

This application claims priority of U.S. Provisional Patent Application No. 60/106,951, filed Nov. 4, 1998.

The subject matter of this application was made with support from the United States Government under National Institutes of Health Grant No. AG 42987-01, Grant No. GM-36812, and Grant No. R37DE04511. The U.S. Government may have certain rights in this invention.

FIELD OF THE INVENTION

The subject invention is directed generally to recombinant keratinocytes and uses thereof, and more particularly to keratinocytes having nucleic acid encoding a human $\beta 3$ integrin subunit introduced therein and to the use of these recombinant keratinocytes in a method of enhancing wound healing in a graft procedure.

BACKGROUN OF THE INVENTION

Throughout this application various publications are referenced, many in parenthesis. Full citations for each of these publications are provided at the end of the Detailed Description. The disclosures of each of these publications in their entireties are hereby incorporated by reference in this application.

It is estimated that in 1992 (US), 35.2 million wounds required major therapeutic intervention (Medical Data International, Inc. 1993). Surgical incisional wounds are performed with aseptic technique, and are closed by primary intention. Most repair and heal uneventfully. Many traumatic wounds and cancer extirpations, however, must be left open to heal by secondary intention. Furthermore, chronic wounds have significant tissue necrosis and fail to heal by secondary intention. It is estimated that 5.5 million people in the US have chronic, nonhealing wounds and that their prevalence is increasing secondary to the increase in age-related diseases, the increase in Acquired-Immune Deficiency Syndrome (AIDS), and the increase of radiation wounds secondary to cancer intervention. In the US approximately 1.5–2.5 million people have venous leg ulcers; 300,000–500,000, diabetic ulcers; and 2.5–3.5 million, pressure ulcers (Callam et al. 1987; Phillips and Dover 1991; Lees and Lambert 1992; Lindholm et al. 1992). These acute and chronic open wounds require long-term care and procedures that include skin grafting and tissue flaps, debridement, frequent dressing changes and administration of pain medications. This care is costly and labor intensive. Furthermore, these wounds have a severe impact on the patients' quality of life. The chronic dermal ulcerations can cost as much as $40,000 each to heal and more disappointing is that 50% reappear within 18 months of healing. Chronic dermal ulcers are also associated with mortality. As many as 21% of patients in intermediate-care facilities with pressure ulcers die (Bergstrom et al. 1994).

Although multiple millions of dollars have been spent on the development of numerous recombinant growth factors (Abraham and Klagsbrun 1996; Heldin and Westermark 1996; Nanney and King 1996; Roberts and Sporn 1996) and organotypic skin replacements (Boyce et al. 1995) for use in open wounds over the past decade, the evidence of cost-effective benefit is meager thus far (Brown et al. 1989; Robson et al. 1992a; Robson et al. 1992b; Phillips et al. 1993).

One approach to promoting wound healing has been the use of grafts. Split-thickness skin grafts removed from one site of a patient and grafted to the wound site on the patient have been used. These split-thickness skin grafts involve costly procedures and considerable pain and suffering for the patient. Another approach in the use of grafts involves the in vitro culturing of keratinocytes removed from a burn victim. The cultured keratinocytes are then grafted back onto the patient (an autograft) (Phillips et al. 1990; Gallico et al. 1984).

Fetal foreskin keratinocytes from one person have been used for grafting onto another person (an allograft) (Phillips et al. 1990). A continuing problem with such allograft procedures is the inability to consistently maintain the keratinocytes at the wound site for the time necessary for stimulation of wound healing. This problem is due in part to the inability of keratinocytes to adhere to fibrin/fibrinogen. If any fibrin/fibrinogen is present at the wound site when the allograft is applied, the keratinocytes do not adhere. Since natural wound healing involves the formation of a fibrin clot, wounds must therefore be thoroughly cleaned of fibrin/fibrinogen (clot) before application of the allograft keratinocytes. This is not an easy or practical task.

Animal keratinocytes (particularly pig keratinocytes) have also been used for human graft procedures (a xenograft). Pig keratinocytes are generally not rejected by humans, but the inability to consistently maintain the pig keratinocytes at the wound site for the time necessary for stimulation of wound healing remains a problem. See Phillips 1998 for a review of developments in biological skin substitutes.

Wound healing occurs as a succession of overlapping states that include inflammatory cell infiltration, re-epithelialization, granulation tissue formation and extracellular matrix (ECM) remodeling. Previous in vivo studies demonstrate that keratinocyte adhesion and motility require expression of the appropriate cell surface receptors for ECM molecules (Woodley 1996; Clark et al. 1985a). Integrins compose one family of such receptors (Adams and Watt 1991). There are over 20 integrins which mediate cell-ECM or cell-cell interactions. Each integrin is a heterodimeric transmembrane protein, consisting of one $\alpha$ and one $\beta$ subunit in a noncovalent complex, which together specify specific ligand binding (Yamada et al. 1996).

In normal human skin, major integrins expressed by keratinocytes are $\alpha 2\beta 1$, $\alpha 3\beta 1$, and $\alpha 6\beta 4$ (Yamada et al. 1996). The $\alpha 2\beta 1$ integrin is a type I collagen receptor while the $\alpha 3\beta 1$ and $\alpha 6\beta 4$ integrins are laminin 5 receptors which form critical adhesions to the basement membrane. In contrast, during re-epithelialization the migrating epidermal cells up-regulate integrins that ligate provisional matrix proteins (Clark 1990) including $\alpha 5\beta 1$ (Juhasz et al. 1993; Larjava et al. 1993; Cavani et al. 1993; Gailit et al. 1994), $\alpha v\beta 5$ (Gailit et al. 1994; Clark et al. 1996a), and $\alpha v\beta 6$ (Larjava et al. 1993; Clark et al. 1996a; Haapasalmi et al. 1996).

Fibrinogen, the major provisional matrix protein present in the wound space immediately after injury (Clark 1996), is a 340,000-Da-hexamer composed of two $A\alpha$, two $B\beta$, and two $\gamma$ chains, and it circulates at approximately 3 gm/liter (Mosesson 1992). Endothelial cells and fibroblasts bind fibrinogen and fibrin through the $\alpha v\beta 3$ integrin in vitro (Newman et al. 1996; Gailit et al. 1997) and invade the fibrin clot in vivo (Clark et al. 1996b; McClain et al. 1996). In contrast, cultured keratinocytes do not produce the $\beta 3$ integrin subunit (Adams and Watt 1991) and therefore do not express the $\alpha v\beta 3$ integrin and do not invade the fibrin-rich clot (Odland and Ross 1968).

The severity of the problem of chronic, nonhealing wounds dictates that continual efforts be made to define new and more effective compositions and/or methods for facilitating wound healing.

SUMMARY OF THE INVENTION

This need is met by the subject invention which provides a recombinant keratinocyte having nucleic acid encoding a human β3 integrin subunit introduced therein. This recombinant keratinocyte is able to express the αvβ3 integrin and therefore is able to adhere to fibrin/fibrinogen. Therefore, when used in a graft procedure, the recombinant keratinocyte is able to adhere to fibrin/fibrinogen present in any fibrin clot in the wound. The need for removal of all fibrin/fibrinogen from the wound site prior to applying the graft is therefore removed.

The invention thus further provides a method of enhancing wound healing in a graft procedure. The method comprises introducing nucleic acid encoding a human β3 integrin subunit into keratinocytes, and using the resulting keratinocytes in a graft procedure.

BRIEF DESCRIPTION OF THE DRAWINGS

These and other features and advantages of this invention will be evident from the following detailed description of preferred embodiments when read in conjunction with the accompanying drawings in which:

FIG. 1A shows a 5 day fixed wound section stained with Masson trichrome. The arrow resides on the tip of the migrating epidermis and points in the direction of migration. The dermis at the wound margin is indicated by the letter (d) and newly forming granulation tissue is noted by (gt). FIG. 1B shows a frozen tissue specimen of a 5 day wound stained for β1 integrin subunit with monoclonal antibody 4B4. FIG. 1C shows a frozen tissue specimen of a 5 day wound stained for αvβ5 integrin with monoclonal antibody P1F6. FIG. 1D shows a frozen tissue specimen of a 5 day wound stained for αvβ3 integrin with monoclonal antibody 23C6. Bright staining αvβ3-positive patches beneath the migrating epidermis are capillary sprouts as previously described (Clark et al. 1996b). FIG. 1E shows a frozen tissue specimen of a 7 day wound stained for αvβ5 integrin with monoclonal antibody P1F6. FIG. 1F shows a frozen tissue specimen of a 7 day wound stained for αvβ3 integrin with monoclonal antibody 23C6. In FIGS. 1A–1D, e denotes wound epidermis and the arrow indicates the direction of migration. Bar=200 $\mu$m in FIG. 1A and 100 $\mu$m in FIGS. 1B–1F;

(FIG. 6A) 5 ng/ml TGF-β2, (FIG. 6B) 10 ng/ml EGF, (FIG. 6C) 80 nM TPA or 10 $\mu$M dibutyryl cyclic AMP, (FIG. 6D) 2 mM MgCl$_2$ or 2 mM CaCl$_2$. Cell adhesion assay Method 1 was used for these investigations (see Methods Section). After the appropriate preincubation (see Methods), 1×10$^4$ viable cells were added to wells coated with either 100 $\mu$g/ml fibrinogen (FG), FGI-9, or fibrin (FB), or 20 $\mu$g/ml D1, E1, type I collagen (COL-I), type IV collagen (COL-IV), fibronectin (FN), or laminin (LN) and incubated for 1 hr. The OD value shown is the total OD minus the BSA control. Adhesion of the treated cells was compared with that of cells kept in control medium (KBM/BSA/PS). Data points are the mean±standard deviation of quadruplicate samples. The results presented here are representative of 3 independent experiments. In FIG. 6A, keratinocyte adhesion to collagen type IV and to laminin was increased by TGF-β (p<0.0001 and <0.01, respectively, as judged by the Student's T test). In FIG. 6B, epidermal cell adhesion to type I collagen was increased by EGF (p<0.01). In FIG. 6C, keratinocyte adhesion to type I and to type IV collagen was increased by TPA (p<0.05 and p <0.0001, respectively). In FIG. 6D, epidermal cell adhesion to type I collagen was increased by MgCl$_2$ and decreased by CaCl$_2$ (p<0.01 and p<0.0001, respectively). Adhesion to type IV collagen and to fibronectin was increased by MgCl$_2$ (p<0.0001 and p<0.05, respectively). Adhesion to laminin was slightly increased by CaCl$_2$ (p<0.01);

In FIG. 7A, keratinocyte adhesion to composites of 100 $\mu$g/ml fibrin or fibrinogen and 10 or 100 $\mu$g/ml fibronectin dried onto plastic wells was compared to adhesion on surfaces coated with the individual proteins. The adhesion assay was done by Method 1 except 200 mM boric acid, pH 4.0 was used to decrease the crystal violet staining of fibrin. Optical density shown here was the difference between the test condition and plates coated with fibrin without cell addition. Data points are the mean±standard deviation of quadruplicate samples. The data shown here are representative of 3 independent experiments. FIG. 7B shows the amount of isotopically labeled fibronectin adsorbed onto plastic wells in the presence or absence of fibrinogen or fibrin. Histograms represent the mean±standard deviation of quadruplicate samples. The data shown are representative of 3 independent experiments. FIG. 7C shows the amount of fibronectin adsorbed onto plastic wells in the presence or absence of fibrinogen or fibrin as judged by an enzyme-linked-streptavidin biotin assay. Histograms represent the mean±standard deviation of quadruplicate samples. The data shown are representative of 3 independent experiments;

FIG. 8A shows phagokinetic migration of human keratinocytes on fibrinogen (FG), collagen (COL), or fibronectin (FN). Keratinocytes were incubated on gold-coated coverslips that were treated with either type I collagen (25 μg/ml), fibronectin (25 μg/ml), fibrinogen (25 μg/ml), or BSA (10 mg/ml). The migration index was determined by measuring the area of gold cleared by the cells (see Methods for details). As judged by the two tail Student's T test there was statistically more keratinocyte migration on collagen and fibronectin compared to the BSA control (p<0.0001 for both comparisons). In contrast, there was statistically less migration on fibrinogen compared to the BSA control (p<0.01). FIG. 8B shows an analysis of keratinocyte-outgrowth from foreskin explants. Biopsies of neonatal foreskin (2×2 mm) were placed onto gels prepared from either fibrin (3 mg/ml) or collagen (2.4 mg/ml). Outgrowth was followed over 3 days (37° C.). Samples were fixed and the percent increase in outgrowth area from the biopsy was determined by image analysis;

FIGS. 11A–11J illustrate cell morphology of the β3 integrin subunit cDNA-transduced keratinocytes (FIGS. 11A–11E) and β-galactosidase cDNA-transduced keratinocytes (FIGS. 11F–11J) (control) after 1 h cell adhesion assay to 100 μg/ml FG (coated at 37° C. overnight) (FIGS. 11A and 11F), 100 μg/ml FB (FIGS. 11B and 11G), 10 μg/ml VN (FIGS. 11C and 11H), 20 μg/ml FN (FIGS. 11D and 11I), and 20 μg/ml Type I collagen (COL-1) (FIGS. 11E and 11J). Cells were fixed with 1% glutaraldehyde for 10 min and stained with 0.1% crystal violet in 0.2 M MES for 20 min.;

DETAILED DESCRIPTION OF THE INVENTION

The subject invention provides a recombinant keratinocyte having nucleic acid encoding a human β3 integrin subunit introduced therein. The keratinocyte can be any keratinocyte, particularly those suitable for graft procedures. Such keratinocytes include, for example, fetal foreskin keratinocytes (which can be used in allograft procedures), a patient's own cultured keratinocytes (which can be used in autograft procedures), and animal keratinocytes (such as pig keratinocytes) (which can be used in xenograft procedures). The removal of keratinocytes from a human subject for culturing in vitro prior to a graft procedure is described more fully below (see "Human Keratinocyte Culture" in Materials and Methods).

The invention further provides a method of enhancing wound healing in a graft procedure, the method comprising: introducing nucleic acid encoding a human β3 integrin subunit into keratinocytes; and using the resulting keratinocytes in a graft procedure. The keratinocytes can, in one embodiment, be transduced using a retroviral vector, the retroviral vector comprising the nucleic acid encoding the human β3 integrin subunit. The graft procedure can be, for example, an allograft procedure, an autograft procedure, or a xenograft procedure.

The following abbreviations are used herein: BSA—bovine serum albumin; EBM—endothelial cell basal media; ECM—extracellular matrix; EGM—endothelial cell growth media; FBS—fetal bovine serum; FGI-9 —fibrinogen fragment I-9; HBSS—Hanks' balanced salt solution; HDMEC—human dermal microvascular endothelial cells; KBM—keratinocyte basal medium; KGM—keratinocyte growth medium; PS—penicillin and streptomycin; TBS—Tris-buffered saline; β-gal—β-galactosidase.

As used herein, a "wound" is intended to include both acute and chronic dermal wounds including, for example, burn wounds, surgical incisional wounds, traumatic wounds, cancer extirpations, radiation wounds, venous leg ulcers, diabetic ulcers, and pressure ulcers. Healing of burn wounds is particularly enhanced using the recombinant keratinocyte and method of the subject invention.

The recombinant keratinocytes of the subject invention can be used to enhance (e.g. improve, increase) wound repair, especially in graft procedures such as allografts, autografts, or xenografts.

Enhancement (e.g. improvement, increasing) of wound healing refers to the traditional sense of wound healing where clean closure of the wound occurs.

Figure 13:
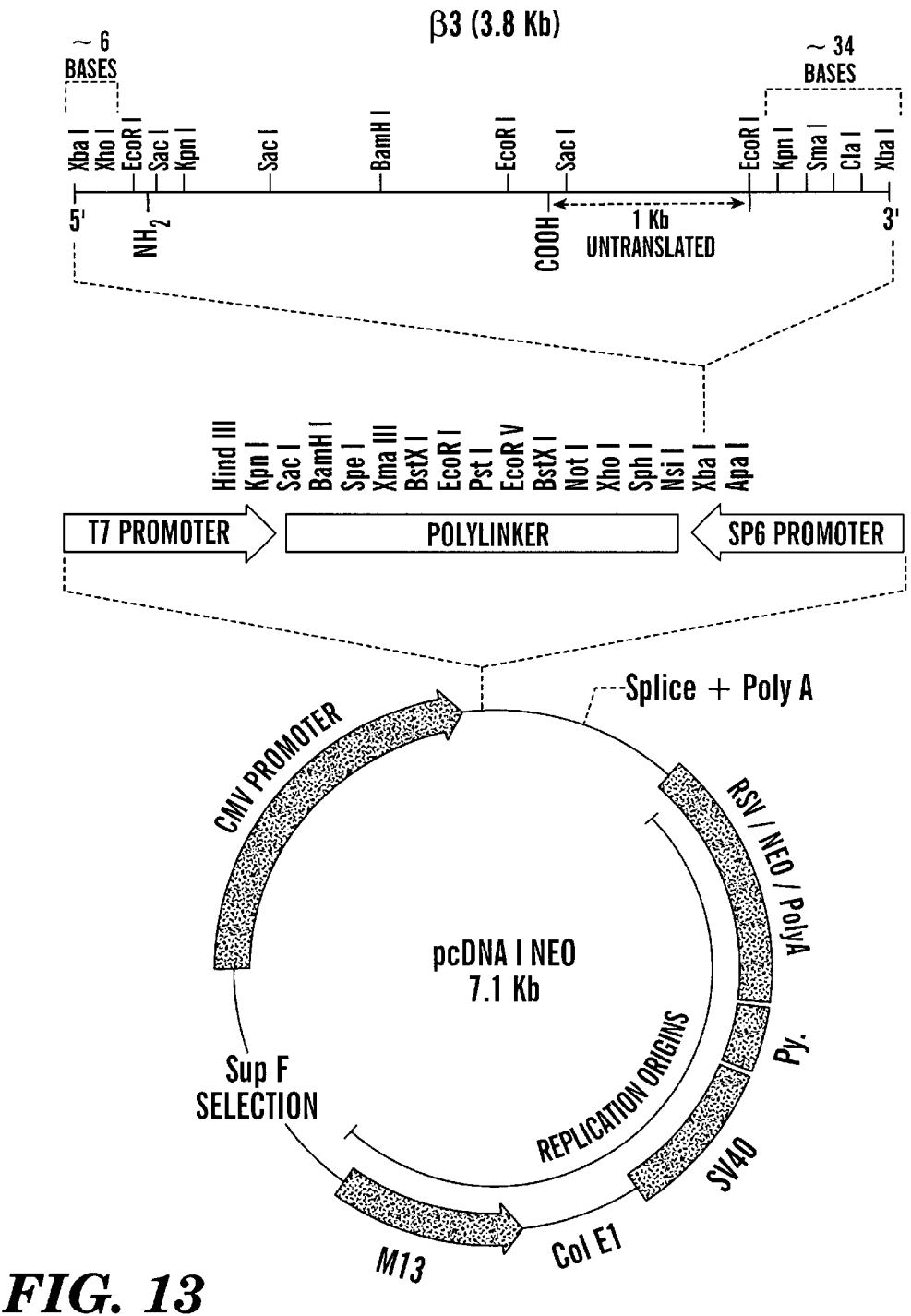
FIG. 13 illustrates the map of pcDNA I NEO with the 3.8 Kb segment encoding the human β3 integrin subunit.

The nucleic acid encoding the human β3 integrin subunit can be obtained from any suitable source. In the Examples which follow, the 3.8 Kb nucleic acid was cut out of the pcDNA I NEO vector (FIG. 13). The nucleic acid molecule encoding the human β3 integrin subunit and the subunit itself have been described, manipulated, and studied (see, for example, Fitzgerald et al. 1987; Danen et al. 1996; Leavesley et al. 1992; Hsu et al. 1998; Simon et al. 1997; Horton 1997; Cheresh 1991; Felding-Habermann and Cheresh 1993). See also U.S. Pat. No. 5,753,230, the contents of which are hereby incorporated by reference. The cDNA could be excised from available vectors which contain the cDNA (such as vectors deposited with the American Type Culture Collection (ATCC), 10801 University Blvd., Manassas, Va. 20110–2209 (http://www.ATCC.org). The vector can be cut with suitable restriction enzymes to obtain the fragment which contains the cDNA encoding the human β3 integrin subunit.

Figure 14:
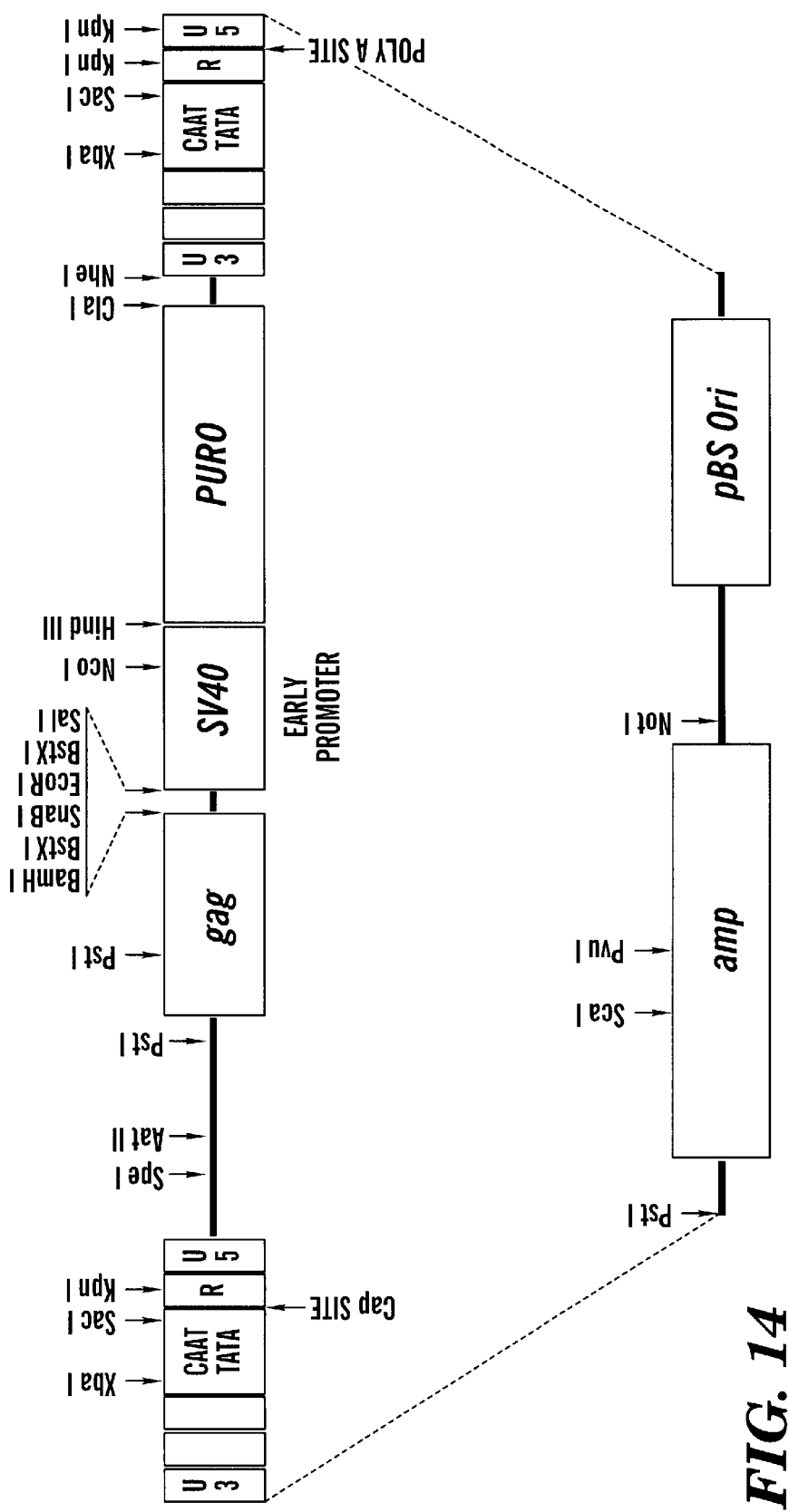
FIG. 14 illustrates the map of the pBabe puro retroviral vector.
Figure 15:
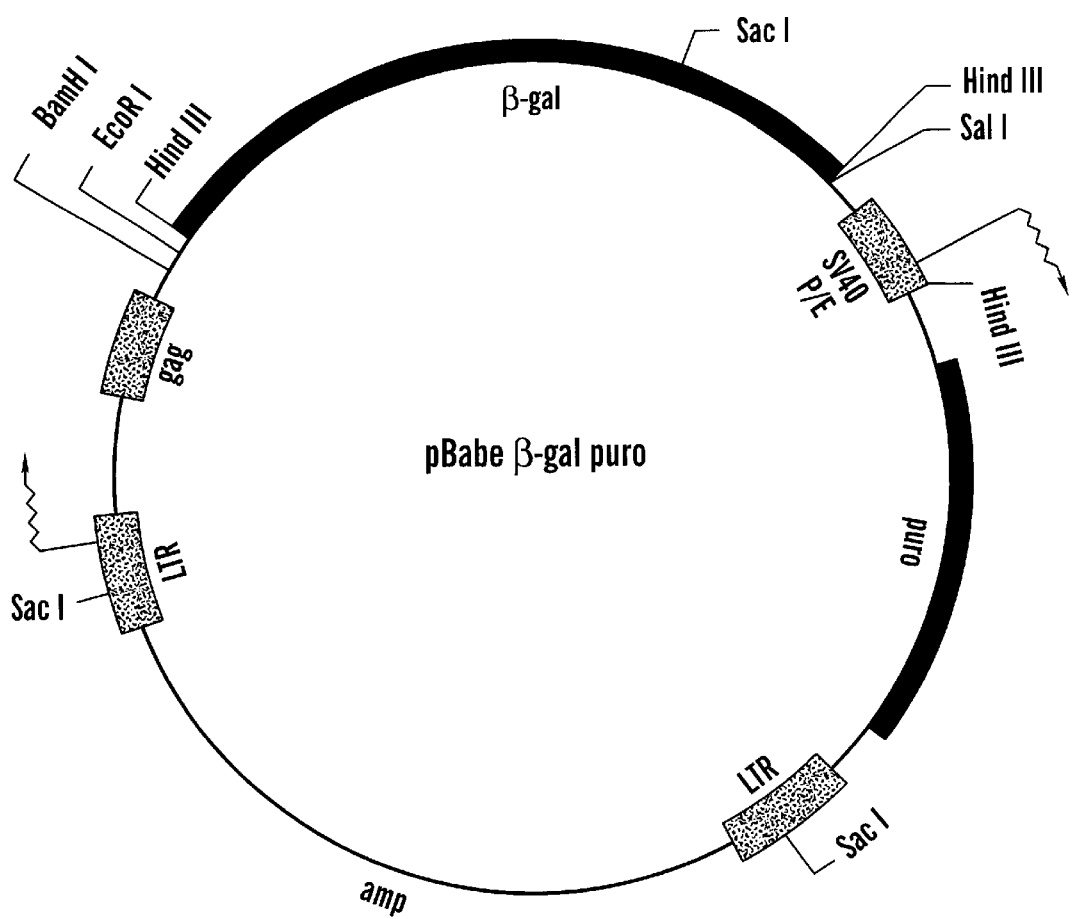
FIG. 15 illustrates the map of the control pBabe β-gal puro retroviral vector.

The nucleic acid molecule encoding the human β3 integrin subunit is introduced into the keratinocytes by any means available in the art. In a presently preferred embodiment, a retroviral vector is used to transduce the keratinocytes in vitro. More particularly, the pBabe puro retroviral vector of Morganstern and Land (1990) (FIG. 14) was cut between the gag and SV40 sites, and the cDNA encoding the human β3 integrin subunit (FIG. 13) was inserted. FIG. 15 shows the map of the control pBabe puro retroviral vector, having β-gal cDNA inserted between the gag and SV40 sites instead of the β3 integrin subunit cDNA. Transduction of the keratinocytes using the BABE vector is described below in "Retrovirus-mediated Transduction of β3 Integrin Subunit cDNA into Normal Human Keratinocytes" in Materials and Methods.

Other methods known in the art can also be used to introduce the nucleic acid encoding the human β3 integrin subunit into keratinocytes. One method is microinjection, in which DNA is injected directly into the cytoplasm of cells through fine glass needles. Alternatively, DNA can be incubated with an inert carbohydrate polymer (dextran) to which a positively charged chemical group (DRAE, for diethylaminoethyl) has been coupled. The DNA sticks to the DEAE-dextran via its negatively charged phosphate groups. These large DNA-containing particles stick in turn to the surfaces of cells, which are thought to take them in by a process known as endocytosis. In another method, cells efficiently take in DNA in the form of a precipitate with calcium phosphate. In electroporation, cells are placed in a solution containing DNA and subjected to a brief electrical pulse that causes holes to open transiently in their membranes. DNA enters through the holes directly into the cytoplasm, bypassing the endocytotic vesicles through which they pass in the DEAE-dextran and calcium phosphate procedures. DNA can also be incorporated into artificial lipid vesicles, liposomes, which fuse with the cell membrane, delivering their contents directly into the cytoplasm. In an even more direct approach, DNA is absorbed to the surface of tungsten microprojectiles and fired into cells with a device resembling a shotgun.

Other viral vectors, especially mammalian vectors, could also be used to introduce the nucleic acid into the keratinocytes. Examples of other viral vectors which have been used to transform mammalian cells include bacteriophage, vaccinia virus, adenovirus, and adeno-associated virus (AAV), to name a few.

Having described the construction of the recombinant keratinocyte of the subject invention, the recombinant keratinocyte can be used in a graft procedure to enhance wound healing. Such graft procedures are well known in the art and include allograft, autograft, and xenograft procedures. A discussion of the methodologies used in such graft procedures can be found in Phillips 1998; Phillips et al. 1990; and Gallico et al. 1984.

The data herein demonstrate that keratinocytes do not adhere to fibrinogen, fibrinogen I-9, D1 and E1 fragments, or fibrin, but adhere well to fibronectin, types I and IV collagen, and laminin. Biologic modifiers known to induce keratinocyte integrin expression or activation failed to induce keratinocyte adhesion to fibrin, fibrinogen or its fragments. Epidermal explant outgrowth and single epidermal cell migration failed to occur on either fibrinogen or fibrin. Furthermore, fibrin and fibrinogen mixed at physiologic molar ratios with fibronectin abrogated the ability of keratinocytes to attach to fibronectin. It was confirmed that human keratinocytes did not express αvβ3 receptor or β3 integrin subunit MRNA using FACS analysis and Northern blot analysis, respectively. Keratinocytes transduced with the β3 integrin subunit cDNA expressed αvβ3 on their cell surface and attached to and spread on fibrin(ogen). β-gal transduced controls did not demonstrate this activity. Furthermore, β3-transduced keratinocyte adhesion to fibrin was inhibited by LM609 monoclonal antibody to αvβ3 in a dose-dependent fashion. From these data, one concludes that normal human keratinocytes cannot interact with fibrin (ogen) or fibronectin-fibrin(ogen) complexes due to the lack of αvβ3. This may be the fundamental reason why migrating epidermis avoids the fibrin clot and dissects the fibrin eschar from wounds.

Materials and Methods

Preparation and Characterization of Fibrinogen, Fibrinogen Degradation Products and RGD Peptides.

Purified peak 1 fibrinogen (Mosesson et al. 1973), fibrinogen fraction I-9 (Mosesson 1974) and fragment D1 (Mosesson et al. 1996) were chromatographically purified from human plasma as described in the cited references. Fragment E was isolated from a stage one plasmin digest of fibrinogen (Meh et al. 1993). Preparations were screened for possible fibronectin contamination by Western blot analysis with polyclonal anti-fibronectin (DAKO, Carpinteria, Calif.). Residual fibronectin was removed from these preparations, when necessary, by adsorption with gelatin-Sepharose 4B (Pharmacia, Piscataway, N.J.). Residual fibronectin as measured by ELISA in the purified preparations was <0.001% wt/wt for peak 1 fibrinogen and E1; undetectable for I-9 and D1. In dose response experiments the ELISA could detect as little as 10 µg/ml fibronectin adsorbed to the wells. The ELISA used goat anti-human fibronectin (Cappel, Durham, N.C.) for the capture antibody, rabbit anti-human fibronectin (GIBCO, Grand Island, N.Y.) as the detection antibody, and goat anti-rabbit IgG alkaline phosphatase conjugate (Cappel) as the secondary antibody. The fibronectin standard was supplied by Biomedical Technologies, Inc. (Stoughton, Mass.). No fibronectin contamination could be detected in any purified fibrinogen preparations by Western blotting. The fibrinogen was >95% clottable.

GRGDSP and GRGESP were purchased from GIBCO BRL (Grand Island, N.Y.).

Human Keratinocyte Culture. Normal human keratinocytes were obtained from neonatal foreskins and grown for two passages with lethally irradiated 3T3-J2 cells (Rheinwald and Green 1975) using a modified medium (Randolph and Simon 1993). At the third passage cells were resuspended in growth media modified by the addition of serum to 10% and DMSO to 10% and subsequently frozen in liquid nitrogen. Keratinocyte cultures were characterized and determined to be >99% pure on the basis of characteristic polygonal morphology and immuno-fluorescence detection of keratin positive cells. For use the frozen cells were quickly thawed at 37° C. and grown in serum-free, low-calcium (0.15 mM) medium KGM from Clonetics Corp. (San Diego, Calif.). All experiments were done using 4th passage-keratinocytes. For the cell adhesion assay, the medium was changed to KBM plus 0.1% Bovine Albumin Fraction V (BSA) from ICN Pharmaceuticals, Inc. (Irvine, Calif.), 100 U/ml penicillin and 100 µg/ml streptomycin from GIBCO BRL (Grand Island, N.Y.) (KBM/BSA/PS) 24 h before the cell harvest.

Human Endothelial Cell Culture. Human dermal microvascular endothelial cells (HDMEC) were isolated from human neonatal foreskins as described by Kubota et al. 1992. Endothelial cell cultures were characterized, and determined to be >99% pure on the basis of characteristic cobble-stone morphology, immunodetection of von Willebrand factor, and uptake of acetylated low density lipoprotein. Experiments were done on HDMEC below passage 8.

Cell Adhesion Assay. Method 1: Adhesion Assay under Wash Conditions. Ninety six-well plates from Flow Laboratories, Inc. (McLean, Va.) were coated with either fibrinogen, fibrinogen I-9, D1, E1; or other matrix proteins including fibronectin, type IV collagen and laminin from GIBCO BRL; type I collagen (Vitrogen 100) from Celtrix Corp. (Santa Clara, Calif.); and BSA from ICN Pharmaceuticals, Inc. Each protein was diluted in 50 mM Tris, pH 7.4, 150 mM $NaCl_{21}$ 0.1% $NaN_3$ (TBS/$NaN_3$) to protein concentrations described in the examples and added to individual wells at a 70 µl volume. After 20 hr at 4° C. for adsorption, all plates were washed with PBS three times using a Nunc Immunowash. Fibrin was made by mixing fibrinogen and 0.1 U/ml thrombin (New York Blood Center) in a solution of TBS/$NaN_3$ plus 10 mM $CaCl_2$ (TBS/$NaN_3$/Ca), and added to individual wells at a 70 µl volume and then incubated at 37° C. for 20 h. These plates were washed two times with TBS/$NaN_3$ and then once with PBS. All wells were blocked with 20 mg/ml BSA, 0.1% $NaN_3$ for 2 hr at 25° C., and then washed again with PBS 3 times. For most cell adhesion assays, $1\times10^4$ viable keratinocytes in 100 µl volume were added to each well and then incubated for 1 hr at 37° C. in 5% $CO_2$, 95% air and 100% humidity. After incubation, the adherent cells were fixed by adding 100 µl of 2% gluteraldehyde for 10 min at 25° C., and then the plates were gently washed with PBS 3 times followed by 5 times with distilled water (Tonneson et al. 1989). The plates were dried and stained with 0.1% crystal violet in 0.2 M MES (Sigma Chemical Co.), pH 6.0 for 20 min at 25° C. with agitation. Plates were washed 5 times in distilled water, and dried. Stained cells were observed under the Nikon phase contrast microscope, and solubilized with 10% acetic acid by shaking for 15 min at 25° C. To determine the number of adherent cells, the solution optical density was measured on a Molecular Devices Microplate reader (Menlo Park, Calif.) at wavebands of 590–450 nm. Results are presented as the mean±standard deviation from 4 replicate wells for each condition assayed.

Cell Adhesion Assay. Method 2: Adhesion Assay under Centrifugal Force Conditions. 20 µl of matrix protein solutions at the concentrations indicated in the examples section were incubated (37° C., 2 hr) on polystyrene sheets as described (Calof and Lander 1991). Sheets were washed, blocked with heat-denatured (65° C.) BSA (10 mg/ml, 20 µl/well) by incubating at 37° C. for 2 hr. Thrombin (5U/ml) was added to wells containing fibrinogen and incubated (37° C., 30 min) and the plates were then washed. Either human keratinocytes or T24 human bladder carcinoma cells (American Type Culture Collection, Manassas, Va.) as a positive control were prelabeled with $^{35}$S-express label 50 µCi/ml for 3 hr and then distributed to wells in 20 µl aliquots of $1.5\times10^5$ cells/ml RPMI plus 1 mg/ml BSA. Test plates were immediately centrifuged up to 53×g and then incubated for 1 hr, at 37° C. to allow cell adhesion to occur. Plates were then inverted, centrifuged (53×g, 8 min) to remove non-adherent cells, fixed in 3% formaldehyde in PBS, dried and radioactivity quantified by phosphoimager analysis using ImageQuant software (Molecular Dynamics). Results are presented as the mean±standard deviation of phosphoimager units from 6 replicate wells.

Measurement of Fibronectin Adsorbed to Plastic Wells in the Absence and Presence of Fibrin(ogen). Isotopic Assay: Wells of 96-well plates (Removawell Strips, Dynatech Laboratories, Inc., Chantilly, Va.) were coated with 70 µl of the appropriate provisional matrix solution: fibronectin alone at either 10 or 100 µg/ml; fibronectin at either 10 or 100 µg/ml plus 100 µg/ml fibrinogen; fibronectin at either 10 or 100 µg/ml plus 100 µg/ml fibrin. Each 100 µg/ml fibronectin contained 0.1078 µCi of I-125 labeled fibronectin, specific activity=7.74 mCi/mg (ICN Biomedicals, Inc., Irvine, Calif.). The solutions of fibronectin with or without fibrin(ogen) were incubated in the plates overnight at 37° C. The next day wells were washed three times with PBS, and the amount of adsorbed FN in the wells were counted by scintillation (LKB 1214 Rackbeta Flexi-Vial).

Measurement of Fibronectin Adsorbed to Plastic Wells in the Absence and Presence of Fibrin(ogen). Enzyme-linked-Streptavidin Biotin Assay: Human plasma fibronectin was conjugated with E2-Link Sulfo-NHS-LC-Biotin (Pierce, Rockfork, Ill.) by the manufacturer's protocol. 96 well plates (Immulon 4, Dynatech Laboratories, Inc.) were coated with 70 µl of various concentrations of biotinylated fibronectin alone or with 100 µg/ml fibrin overnight at 37° C. The next day plates were washed three times with PBS. To block residual protein binding sites on the plastic surface each well was incubated with 2% BSA for 2 hr at room temperature. Next wells were washed with PBS plus 0.02% Tween 20 (PBS Tween) three times and then incubated with 100 µl of alkaline phosphatase conjugated Streptavidin (Vector Laboratory) at a dilution of 1:10,000 for 30 min. at room temperature. After washing 3 times with PBS Tween, the wells were incubated with Fast Red® (BioGenex, San Ramon, Calif.) for 30 min. at room temperature. The optical density of the solution was read on a Molecular Devices Microplate reader at 405 nm.

Effects of TGF-β, EGF, TPA, dibutyryl cyclic AMP, and Divalent Cations on Human Keratinocyte Adhesion to Fibrinogen, FG I-9, D1, E1, Fibrin and other ECM Proteins Effects of TGF-β and EGF were examined by incubating cells with or without TGF-β1 (Celtrix Corp, Santa Clara, Calif.), TGF-β2 (Genzyme Tissue Repair, Framingham, Mass.), or EGF (Clonetics) in KBM/BSA/PS for 24 hr before the cell harvest and also during the 1 hr cell adhesion assay by Method 1. The effects of TPA, dibutyryl cyclic AMP and divalent cations ($MgCl_2$, $CaCl_2$) were examined by adding these reagents to the KBM/BSA/PS medium during the 1 h cell adhesion assay only. The dose of each reagent indicated in the examples was chosen based on previously reported data (Freed et al. 1989; Chen et al. 1993; Iwasaki et al. 1994; Lange et al. 1994; Fujii et al. 1995; Hertle et al. 1995).

Cell Migration Assay. Method 1: Modified Phagokinetic Migration Assay of Human Keratinocytes. Colloidal gold solution was prepared by mixing 3 ml 36.5 mM $Na_2CO_3$, 0.9 ml 14.5 mM $HAuCl_4$ (Sigma Chemical Company) and 5.5 ml $H_2O$, heated to boiling and adding 0.9 ml of 0.1% formaldehyde. Acid-washed 12 mm glass coverslips were dipped sequentially in 1% BSA and 100% ethanol and then dried. Coverslips were placed in wells of a 24-well plate, and incubated 45 min with 0.5 ml of freshly prepared gold colloid solution, washed once with PBS, overlaid with 75 $\mu$l of PBS solution containing ECM proteins, incubated for 2 hr at 37° C. in a humidified environment, washed once with PBS, and then placed in wells of a 24 well plate containing 0.5 ml KGM medium.

Human foreskin keratinocytes were either purchased from Clonetics Corp. (San Diego, Calif.) or were prepared from foreskins as described above (Rheinwald and Green 1975). In either case cells were maintained in KGM (Clonetics Corp.) prior to assays. Both preparations yielded identical experimental results. Cells were harvested by trypsinization, resuspended in KGM ($2 \times 10^4$ cells/ml) and 0.5 ml of the suspension added to each well. After 16 to 18 hr of incubation the coverslips were fixed in situ by underlaying the medium with 3.7% formaldehyde in 10% sucrose, washed once with $H_2O$ and stained with 3 $\mu$M ethidium homodimer (Molecular Probes, Eugene, Oreg.) solution.

The extent of cell migration was determined by measuring the area of gold cleared by the cells. Three to five fields per coverslip were photographed under darkfileld and fluorescent illumination using a 5× objective on a Zeiss Axioscop equipped with a Photometrics CCD camera. The percentage of total area cleared by the cells was determined by tracing each phagokinetic track and calculating the sum of these areas using an image processing program (NIH Image software). This "cleared area" was divided by the total area of the field to give the "percent cleared". Because the number of cells per field varied, the "normalized migration index" was calculated by dividing the "percent cleared" by the number of cells per field as visualized by ethidium homodimer staining. Each experimental point represents the mean of 3 to 5 fields and error bars are the SEM.

Cell Migration Assay. Method 2: Keratinocyte Outgrowth into Fibrin or Collagen Gels. Human foreskins were obtained from anonymous donors from the Beth Israel Hospital Obstetrics Department. Foreskin biopsies (~2 mm diameter) were placed onto preformed gels (0.5 ml) of type I (95%) and type III (5%) bovine collagen (2.4 mg/ml Vitrogen, Collagen Corp.) or fibrin (3 mg/ml purified human fibrinogen to which thrombin 5 U/ml was added) in DMEM containing 10% fetal bovine serum (FBS), depleted of all plasma fibronectin by duplicate passages over a gelatin-affinity column (Van De Water et al. 1981). Explants were incubated 3 days (37° C.), fixed (3% paraformaldehyde in PBS), stained and the area of epidermal outgrowth determined by photographing the explants and quantifying with NIH Image. The increase (%) in outgrowth area was calculated as: [(Area of total explant at day 3—area of original explant) /area of original explant]×100%.

FACS Analysis for β3 Integrin Subunit and αvβ3 Integrin. Cultures of normal adult human keratinocytes and fibroblasts were analyzed for the cell surface expression of β3 integrin subunit and αvβ3 integrin by quantitative flow cytometry as described previously (Gailit et al. 1996; Gailit and Clark 1996). The monoclonal antibody 7E3, against the β3 subunit, was supplied by Barry Coller (Mount Sinai Medical Center, N.Y.) (Charo et al. 1987; Coller 1985). The monoclonal antibody LM609, against αvβ3 integrin was kindly provided by David Cheresh (Research Institute of Scripps Clinic, La Jolla, Calif.) (Cheresh and Spiro 1987).

RNA Isolation and Northern Blot Analysis for β3 Subunit mRNA. Total RNA was isolated from monolayers of human keratinocytes or microvascular endothelial cells (Tonnesen et al. 1989) using a modification of the guanidinium thiocyanate method (Chomczynski and Sacchi 1987). For Northern blot hybridization, 5–10 $\mu$g of total RNA was treated with glyoxal/DMSO, separated by electrophoresis on a 1% agarose gel in 10 mM phosphate buffer, pH 7.0, and transferred to nitrocellulose membrane as previously described (Xu and Clark 1996). Ethidium bromide (0.5 $\mu$g/ml) was included in the gel to monitor equal loading by the quantity of 18s and 28s ribosomal RNA present. CDNA probes were labeled with [$\alpha$-$^{32}$P]dCTP by the random primer procedure (Du Pont New England Nuclear, Boston, Mass.). Oligonucleotide probes were end-labeled with [$\gamma$-$^{32}$P]ATP (Du Pont NEN) and polynucleotide kinase (Boehringer Mannheim). The probes were allowed to hybridize to the filter-bound RNA in QuickHyb solution (Stratagene, La Jolla, Calif.) for 3 hr at 68° C. and washed according to manufacturer's protocol. Films (Kodak X-Omat AR) for autoradiography were processed at −80° C. for optimal exposure. Human β3 cDNA was the generous gift of Dr. Shintaro Suzuki at the Doheny Eye Institute (Los Angeles, Calif.) (the CDNA was as described in Suzuki et al. 1990) and oligonucleotide complementary to 28s ribosomal RNA was purchased from Clontech (Palo Alto, Calif.).

Porcine Cutaneous Wound Model. Full-thickness excisional wounds were made by an 8 mm circular punch into the paravertebral skin of a Yorkshire pig; dressed with TEGADERM™, a polyurethane occlusive dressing; and harvested 1–10 days later as previously described (Welch et al. 1990). Specimens from all wound sites were bisected vertically. One half of each specimen was fixed in formalin, paraffin embedded, sectioned at 5 $\mu$m, and stained with Masson trichrome to delineate the relationship of the migrating epidermis and clot during wound repair. The other half was frozen in liquid nitrogen for immunofluorescence studies aimed at determining whether αvβ3 integrin was present or absent in the epidermis during re-epithelialization of cutaneous wounds.

Immunofluorescence Studies. Frozen sections were prepared for immunofluorescence as previously described (Folkvord et al. 1989). All antibodies were used at dilutions that gave maximal specific fluorescence and minimal background fluorescence on frozen tissue specimens. Bound antibody was detected by the avidin-biotin-complex (ABC)

technique as previously described (Folkvord et al. 1989). Immunofluorescence controls included sections stained with an irrelevant monoclonal antibody instead of the primary antibody, as well as sections in which either the primary and/or secondary antibody (ies) was omitted from the staining procedure. Monoclonal antibodies 7G2 specific for the integrin subunit $\beta 3$ (Gresham et al. 1989); 23C6 specific for the $\alpha v\beta 3$ complex (Horton et al. 1985); P1F6 (Gibco BRL, Grand Island, N.Y.) and P3G2 specific for the $\alpha v\beta 5$ complex (Wayner et al. 1991); and 4B4 (Coulter, Hileah, Fla.) specific for the $\beta 1$ subunit (Matsuyama et al. 1989) were used to detect the integrins of interest. Although these antibodies are known to be specific for distinct integrins in human tissues, these antibodies were tested for their ability to precipitate the appropriate integrin from cultured pig fibroblasts using previously described methods (Gailit et al. 1993). LM609, an anti-$\alpha v\beta 3$ complex blocking antibody (Cheresh and Spiro 1987), was .also used in these immunofluorescence studies but it failed to detect $\alpha v\beta 3$ on the tips of capillary sprouts (Clark et al. 1996b), a critical internal control.

Vectashield mounting medium (Vector Laboratories, Burlingame, Calif.) was used to retard quenching. Slides were photographed on 35 mm Tmax 400 film (Eastman Kodak, Rochester, N.Y.) using a Nikon Microphot FXA epifluorescence microscope equipped with a halogen light source, a 470–490 nm excitation filter and a 515 nm barrier filter for fluorescein emission. The filters selected excluded cross excitation resulting in pure yellow/green fluorescein.

Retrovirus-mediated Transduction of $\beta 3$ Integrin Subunit CDNA into Normal Human keratinocytes. The BABE retroviral vector is derived from Molony murine leukemia virus and contains a selectable marker, puromycin (Morgenstern and Land 1990). The 3.8 kb cDNA containing the full length human $\beta 3$ integrin subunit (FIG. 13) (Fitzgerald et al. 1987) was inserted into PBABE puro at the Sall site (FIG. 14). Infectious recombinant retrovirus was generated in $\Psi$ CRE cells followed by transinfection into GP+envAM12 cells according to established protocol (Miller 1992). GP+envAM12 producers (Markowitz et al. 1988) were selected with puromycin (Sigma Chemical Co.) and individual clones tested. The clone with the highest titer, as measured in 3T3 cells, $(1\times 10^7$ CFU/ml) was used. A BABE retrovirus encoding the gene for $\beta$-galactosidase ($\beta$-gal) was used as a control (Ghazinzadeh et al.1997) (FIG. 15). Keratinocytes were transduced (Garlick et al. 1991) and expanded in a serum-containing medium (Wu et al. 1982) without the use of puromycin. Marker rescue assay for helper virus was negative. Protein expression of $\alpha v\beta 3$ on the cell surface was screened by avidin-biotin immunofluorescence technique using 23C6 specific for $\alpha v\beta 3$ (Horton et al. 1985), biotinylated anti-mouse IgG (Vector, Burlingame, Calif.) and fluorescein streptavidin (Vector). FACS analysis was used to confirm positive cultures.

Cell adhesion assay was done by Method 1. Vitronectin was purchased from Sigma Chemical Co.. Adhesion of $\beta 3$ cDNA-transduced keratinocytes to fibrin(ogen) was dependent on cell density and was best up to 50–60% confluence of the cultures. Therefore, 4th passage-keratinocytes were cultured in KGM for 3–4 days up to 50–60% confluence. Medium was changed to KBM 24 h prior to the cell harvest. $\beta$-gal cDNA-transduced keratinocytes were used as control cells. Stained cells were photographed with a Nikon inverted microscope at 200× magnification. Inhibition assay of the cell adhesion was done by incubating cells with various concentrations of LM609 (monoclonal antibody to $\alpha v\beta 3$), anti-$\alpha 5\beta 1$ monoclonal antibody (provided by Dr. Kenneth Yamada of the National Institute of Dental Research in Bethesda, Md.), anti-human FN polyclonal antibody (Cappel), and normal mouse IgG1 (Sigma Chemical Co.) as a control for 30 min at 25° C. before adding cells to the wells.

Figure 1A:
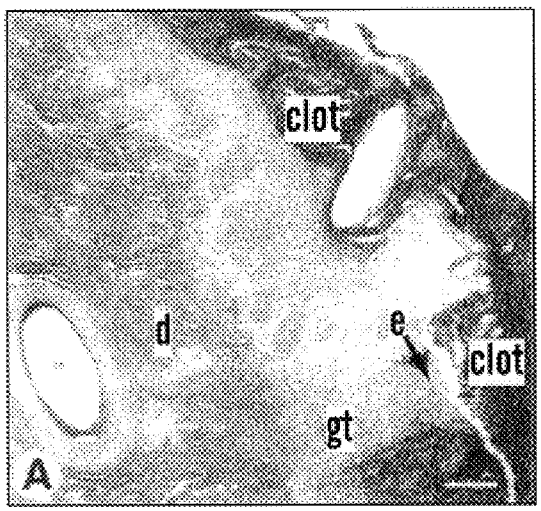
FIGS. 1A–1F illustrate histology and integrin expression of re-epithelializing porcine wounds. Full-thickness paravertebral skin wounds were harvested on day 5 or 7 and bisected. One half was formalin fixed and stained with Masson trichrome and the other half was quick frozen in OTC with liquid nitrogen.
Figure 1B:
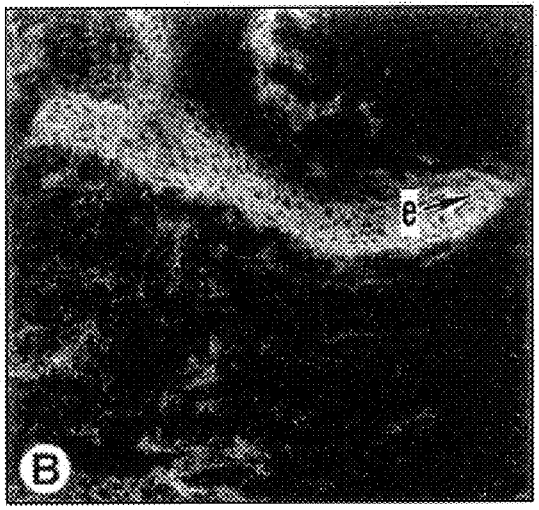
Figure 1C:
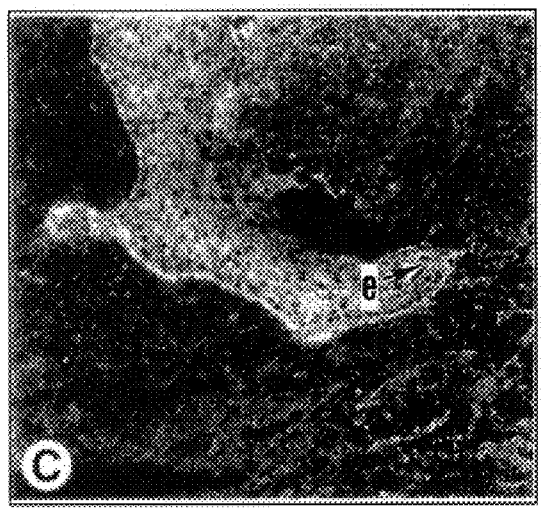

EXAMPLE I
The Migrating Epidermis of Wounds Avoids the Fibrin Eschar and Fails to Express the Fibrin(ogen) receptor $\alpha v\beta 3$ In early cutaneous wound healing the migrating epithelial tongue descended along the dermal wound margin and newly forming granulation tissue separating the fibrin clot from viable tissue (FIG. 1A). The migrating epidermis expressed markedly increased PI integrins (FIG. 1B) as previously reported (Clark 1990; Juhasz et al. 1993; Cavani et al. 1993; Gailit et al. 1994), the $\alpha v\beta 5$ vitronectin receptor (FIGS. 1C and 1E) (Gailit et al. 1994; Clark et al. 1996a), but no $\alpha v\beta 3$ integrin as judged by monoclonal antibody 23C6 (FIGS. 1D and 1F) and no $\beta 3$ subunit as judged by monoclonal antibody 7G2 (data not shown). Importantly 23C6 and 7G2 detected remarkable $\alpha v\beta 3$ and $\beta 3$ subunit staining, respectively, on the tips of capillary sprouts in the same 5 day wound tissue sections where the epidermis was not stained (FIG. 1C). Both porcine (FIGS. 1A–1F) and human (not shown) wound epidermis failed to express $\alpha v\beta 3$, while both expressed $\alpha v\beta 5$ during the first week of healing (FIGS. 1C and 1E) (Gailit et al. 1994; Clark et al. 1996a). The dissection of the fibrin clot from the wound space continues until the fibrin eschar is sloughed from the wound. Surprisingly, the mechanism by which the migrating epidermis avoids the fibrin clot has not been previously addressed. Therefore, the interactions of human keratinocytes with fibrin, fibrinogen and its fragments were investigated.

Figure 3A:
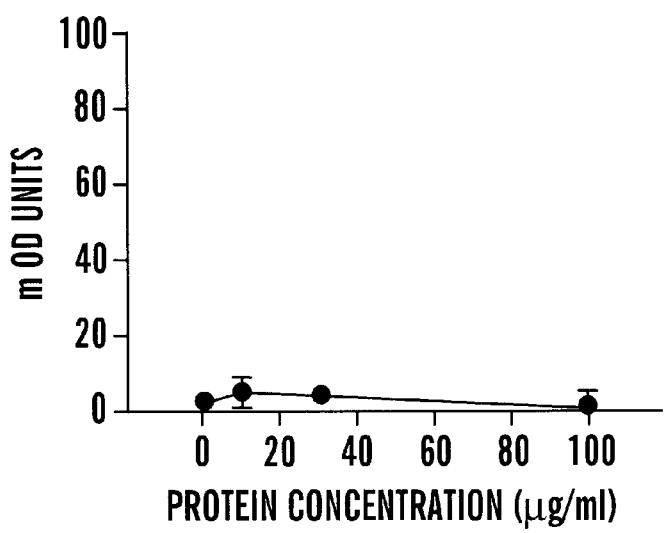
FIGS. 3A and 3B illustrate fibrin dose response of the adhesion of human keratinocytes (FIG. 3A) and microvascular endothelial cells (FIG. 3B). The adhesion assay was done by Method 1 except 200 mM boric acid, pH 4.0 was used to decrease the crystal violet staining of fibrin. Optical density shown here was the difference between the test condition and plates coated with fibrin without cell addition. Data points are the mean±standard deviation of quadruplicate samples. The data shown here are representative of 3 independent experiments.
Figure 3B:
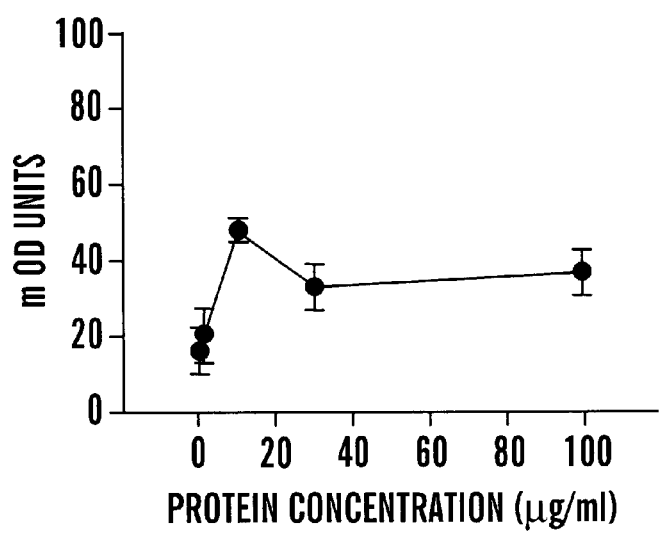

EXAMPLE II
Human Keratinocytes Fail to Interact with Fibrinogen, FGI-9, D1, E1 and Fibrin but Adhere to other ECM Proteins Human keratinocyte adhesion to various ECM proteins was determined using the cell adhesion assay Method 1. As shown in FIGS. 2A–2H, human keratinocytes failed to adhere to fibrinogen or its fragments at any concentration examined. In contrast, keratinocytes adhered well to type I collagen, fibronectin, type IV collagen and laminin in a dose-dependent manner. Keratinocyte adhesion was maximum at 10 $\mu$g/ml of type I collagen and fibronectin, and at 20 $\mu$g/ml of type IV collagen and laminin (FIGS. 2A–2H). Keratinocytes adhered better to type I collagen and fibronectin than to type IV collagen and laminin. These results were consistent with previously reported results (Clark et al. 1985a; Kubo et al. 1987). Human keratinocytes also did not adhere to fibrin fibrils (FB) (FIGS. 3A and 3B). Since it has recently been demonstrated that human microvascular endothelial cells attach to fibrin using the same assay as used here for keratinocytes (Newman et al. 1996), a direct comparison of the two cell types is presented. Visual examination of the assay plates coated with BSA, fibrinogen or fibrin confirmed that negligible (<2%) keratinocytes bound to these substrata.

Figure 4A:
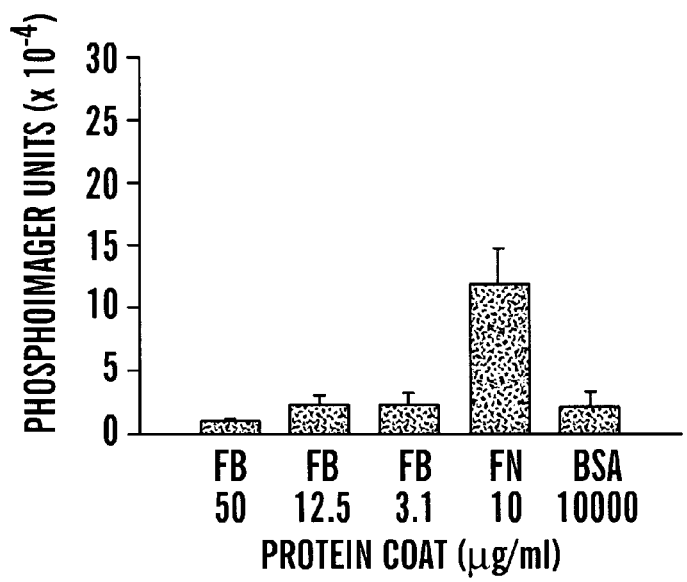
FIGS. 4A and 4B illustrate keratinocyte and T24 bladder carcinoma cell adhesion to fibrin (FB) and fibronectin (FN). Human keratinocytes (FIG. 4A) or T24 human bladder carcinoma cells (FIG. 4B) were applied to wells (3×10$^3$ cells in 20 $\mu$l) precoated with fibrinogen at the indicated concentrations ($\mu$g/ml) followed by thrombin (5 U/ml, 30 min), plasma fibronectin (10 $\mu$g/ml), or BSA (10 mg/ml). Cells were incubated (37° C., 1 hr), inverted, and centrifuged (53×g, 8 min) to dislodge non-adherent cells. Data are presented as the mean±standard deviation of cell-associated radioactivity (phosphoimager units ×10$^{-4}$) bound to the plates. Binding of T24 cells to 50 $\mu$g/ml fibrinogen and to fibronectin was statistically greater than keratinocyte binding to these surfaces (p<0.01 and <0.0001, respectively) as judged by the Student's T test.
Figure 4B:
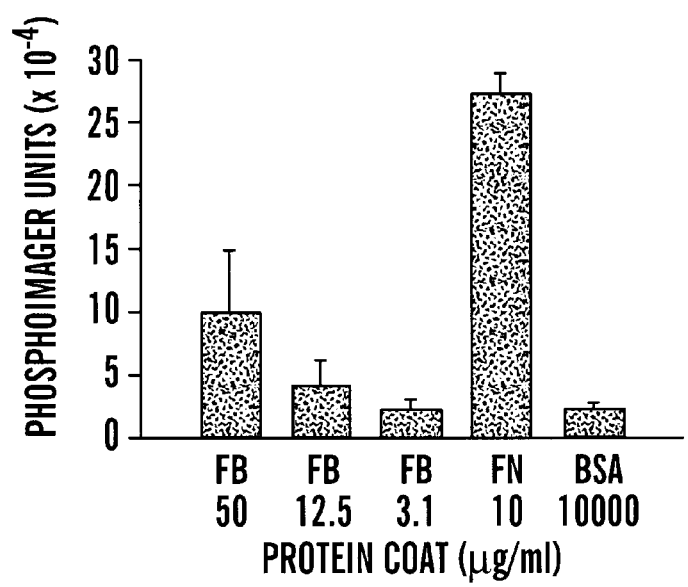

EXAMPLE III
Bladder Carcinoma T24 Cells, but not Human Keratinocytes, Adhere to Fibrin and Fibronectin in a Centrifugal Force Assay To confirm the inability of keratinocytes to adhere to fibrin, a second adhesion assay was used in which centrifugal force substituted for washing off nonadherent cells. In this assay human keratinocytes again failed to adhere to fibrin over a range of coating concentrations from 3.1, 12.5 and 50 $\mu$g/ml (FIG. 4A), but adhered well to fibronectin at 10 μg/ml (FIG. 4A). By contrast, human bladder carcinoma T24 cells, which express αvβ3 (Senger et al. 1994), adhered in a concentration dependent fashion to fibrin as well as to fibronectin (FIG. 4B). Experiments in which plates were centrifuged at higher force (133×g instead of 53×g) yielded identical results for keratinocytes. Somewhat lower, albeit significant, binding was observed for T24 cell attachment to fibrin at this higher "g" force (data not shown). Therefore, these results confirmed the inability of human keratinocytes to adhere to fibrin under conditions of uniform centrifugal force.

EXAMPLE IV
Human Keratinocytes Fail to Express Cell Surface β3 Integrin Subunit and αvβ3 Integrin As shown in Table 1, FACS analysis revealed no significant expression of the β3 integrin subunit on keratinocytes. The monoclonal antibody 7E3 that recognizes integrin complexes containing the β3 subunit (Charo et al. 1987; Coller 1985) and the monoclonal antibody LM 609 specific for integrin αvβ3 (Clark et al. 1996b; Cheresh and Spiro 1987; Brooks et al. 1994) both failed to detect the β3 subunit or αvβ3 integrin on the keratinocyte cell surface. In contrast, adult human dermal fibroblasts expressed clearly detectable levels of the β3 subunit and αvβ3 integrin.

EXAMPLE V
Human Keratinocytes Fail to Express β3 Subunit MRNA

Figure 5:
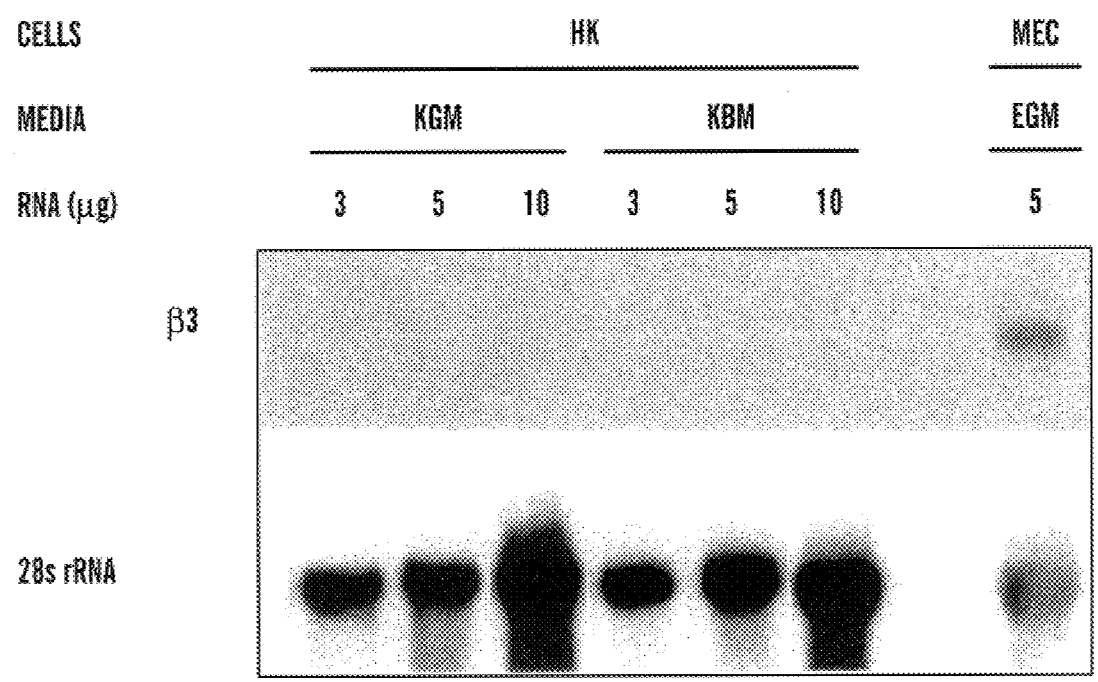
FIG. 5 illustrates a Northern blot analysis of β3 integrin subunit. Total RNA (3, 5, 10 $\mu$g/ml) from monolayers of human keratinocytes cultured in KGM or KBM or microvascular endothelial cells cultured in EGM was probed with human β3 integrin subunit cDNA. The amount of RNA was monitored by UV light examination of ethidium bromide stained gel and equal loading was confirmed by hybridization of the same blot with $^{32}$P-labeled probe for 28s ribosomal RNA.

Keratinocytes either in KGM or KBM failed to express β3 subunit mRNA (FIG. 5) in agreement with previously published data (Adams and Watt 1991). In contrast, human microvascular endothelial cells in EGM (Clonectics Corp.) expressed β3 subunit (FIG. 5) as previously described (Enenstein et al. 1992; Klein et al. 1993; Sepp et al. 1994).

Figure 6B:
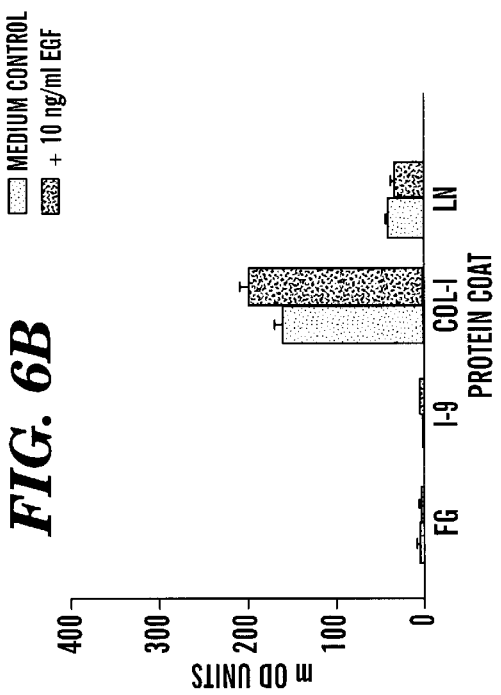
FIGS. 6A–6D illustrate the effects of TGF-β, EGF, TPA, dibutyryl cyclic AMP and divalent cations on human keratinocyte adhesion to fibrin, fibrinogen, its fragments and other ECM proteins.
Figure 6D:
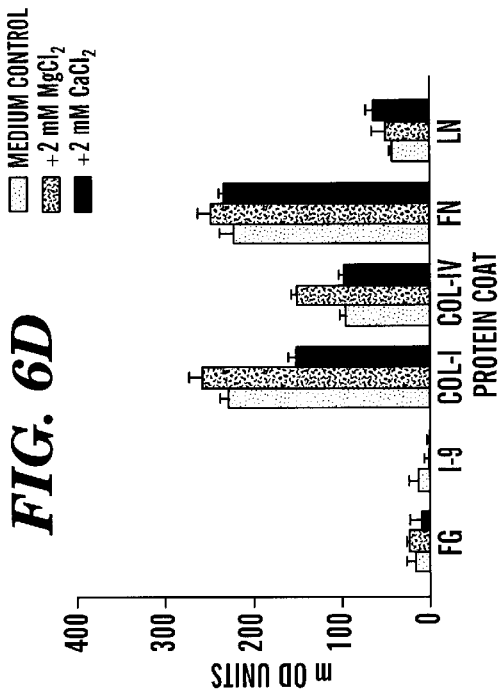
Figure 6A:
Figure 6C:
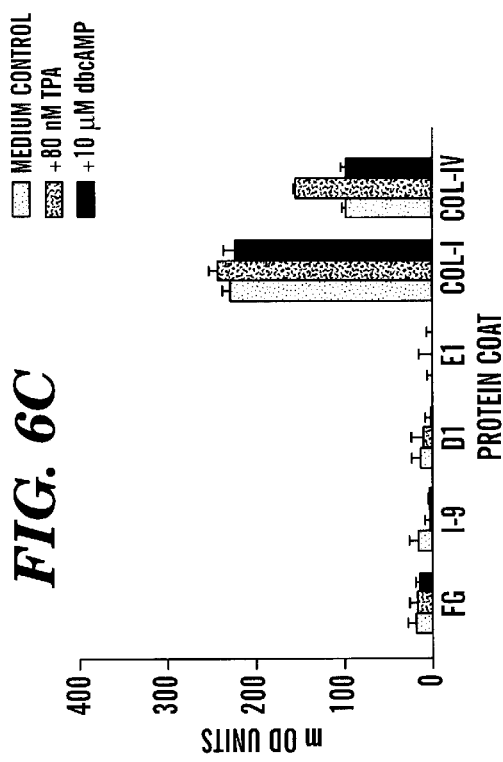

EXAMPLE VI
TGF-β, EGF, TPA, dibutyryl cyclic μMP and Divalent Cations Fail to Induce Human Keratinocyte Interaction with Fibrinogen, its Fragments, or Fibrin Since TGF-β, EGF, TPA, dibutyryl cyclic AMP and divalent cations are known to be inducers or activators of integrin receptors (Freed et al. 1989; Chen et al. 1993; Iwasaki et al. 1994; Lange et al. 1994; Fujii et al. 1995; Hertle et al. 1995), the effects of these reagents on human keratinocyte adhesion to fibrinogen, its fragments, fibrin and other ECM proteins were examined. TGF-β2 at 5 ng/ml failed to induce human keratinocyte adhesion to fibrinogen, its fragments or fibrin, while it significantly increased adhesion to type IV collagen and laminin (FIG. 6A). The adhesion to fibronectin was increased 2-fold by TGF-β2 (data not shown). TGF-β1 at 5 ng/ml and TGF-β2 at 10 ng/ml gave essentially the same results (data not shown) as 5 ng/ml TGF-β2 (FIG. 6A). EGF at 10 ng/ml failed to induce human keratinocyte adhesion to fibrinogen, FGI-9 or fibrin as well as to laminin. EGF did, however, increase adhesion to type I collagen (FIG. 6B) in agreement with previous reports that EGF increases keratinocyte α2β1 integrin, a collagen receptor (Chen et al. 1993). 80 nM TPA failed to induce human keratinocyte adhesion to fibrinogen, FGI-9, or fragments D1 or E1, but increased adhesion to type I and to type IV collagen (FIG. 6C) in concert with previous data that PMA induces the α2β1 collagen receptor gene (Xu et al. 1996). Dibutyryl cyclic μMP did not affect adhesion of human keratinocyte to any matrix protein (FIG. 6C). Neither 2 mM $MgCl_2$, nor 2mM $CaCl_2$, induced human keratinocyte adhesion to fibrinogen or FGI-9. In contrast, 2 mM $MgCl_2$ increased keratinocyte adhesion to types I and IV collagen, while 2 mM $CaCl_2$ decreased keratinocyte adhesion to type I collagen (FIG. 6D). Lack of keratinocyte attachment to fibrinogen, FGI-9 and fibrin under all these conditions was always confirmed by visual examination.

Figure 7A:
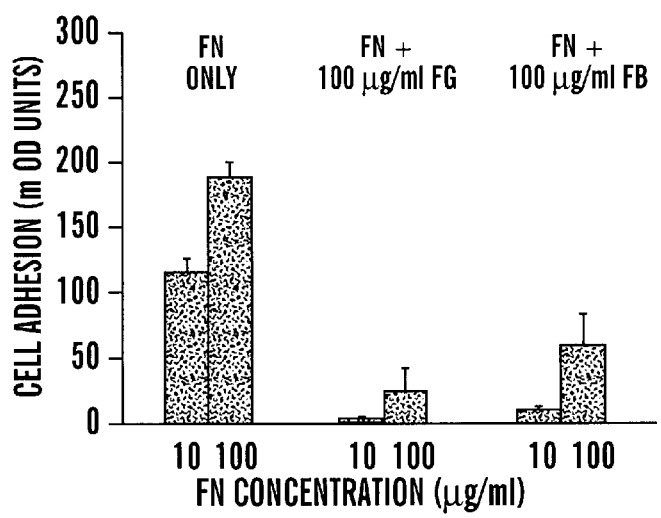
FIGS. 7A–7C illustrate the failure of keratinocytes to interact with fibronectin/fibrin(ogen) composites.
Figure 7B:
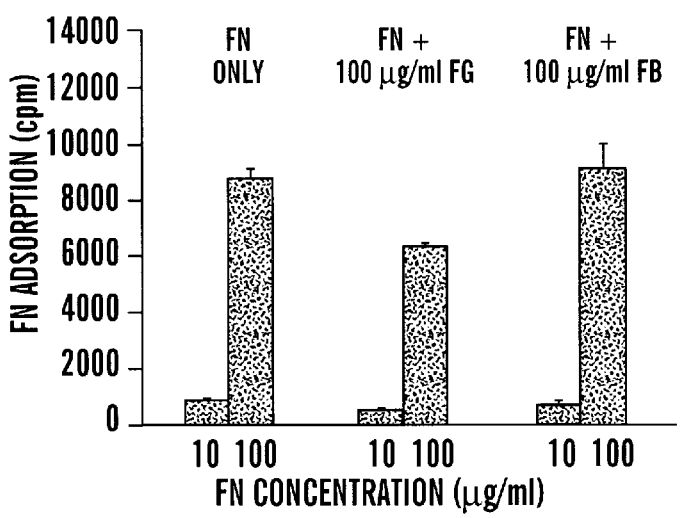
Figure 7C:
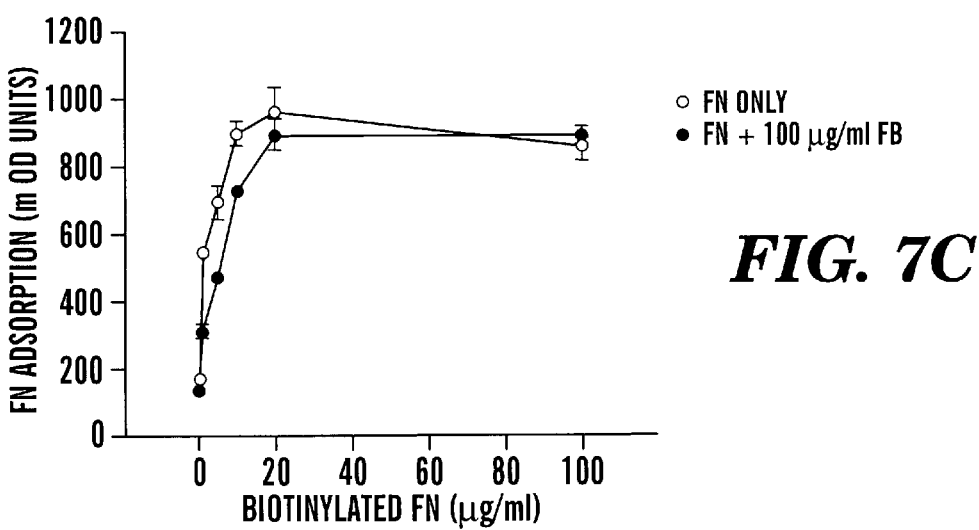

EXAMPLE VII
Keratinocytes Fail to Interact with Physiologic Composites of Fibronectin with Fibrinogen or Fibrin Since in vivo fibrin clots contain substantial fibronectin (~1:10 molar ratio with fibrin) the ability of keratinocytes to adhere to fibronectin-fibrin or—fibrinogen complexes was investigated. At physiologic molar ratios fibrinogen and fibrin completely abrogated the ability of normal human keratinocytes to interact with fibronectin (FIG. 7A). Even at 1:1 molar ratios keratinocyte adhesion to fibronectin-fibrin or fibronectin-fibrinogen composites was far less than adhesion to fibronectin alone (FIG. 7A). These data were not attributable to less fibronectin being adsorbed to plastic surfaces in the presence of fibrin or fibrinogen. In fact, fibronectin adsorption to plastic surfaces was little affected by either fibrinogen or fibrin as judged by radioisotope or ELISA studies (FIGS. 7B and 7C, respectively).

EXAMPLE VIII
Keratinocytes Fail to Migrate on Fibrinogen and Migrate Poorly on Fibrin Clots Migration of keratinocytes was observed in two settings, a planar surface and on three-dimensional protein gels. In the first assay, migration of individual cells was analyzed by quantifying the extent to which cells "cleared" a lawn of gold particles, the so-called phagokinetic assay. In the second assay, the sheet migration of epidermal keratinocytes, growing out of a tissue fragment, was analyzed.

Figure 8A:
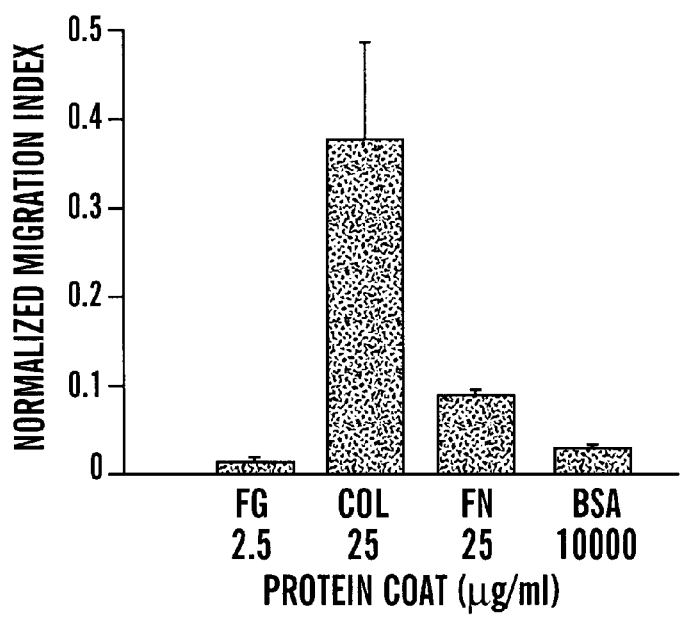
FIGS. 8A and 8B illustrate keratinocyte migration on fibrinogen, fibrin, type I collagen and fibronectin.

Phagokinetic Migration Assay: Significant keratinocyte migration was observed on gold-treated coverslips coated with type I collagen or with plasma fibronectin (FIG. 8A). Consistently more robust migration was observed on collagen than fibronectin, shown here at 25 μg/ml, a concentration that saturated the coverslips. No significant difference in keratinocyte migration was noted when cells were plated on plasma or cellular fibronectin, or on a mixture of fibronectin variants (data not shown). Keratinocytes never migrated on fibrinogen (25 μg/ml) in the presence or absence of thrombin (FIG. 8A).

Figure 8B:
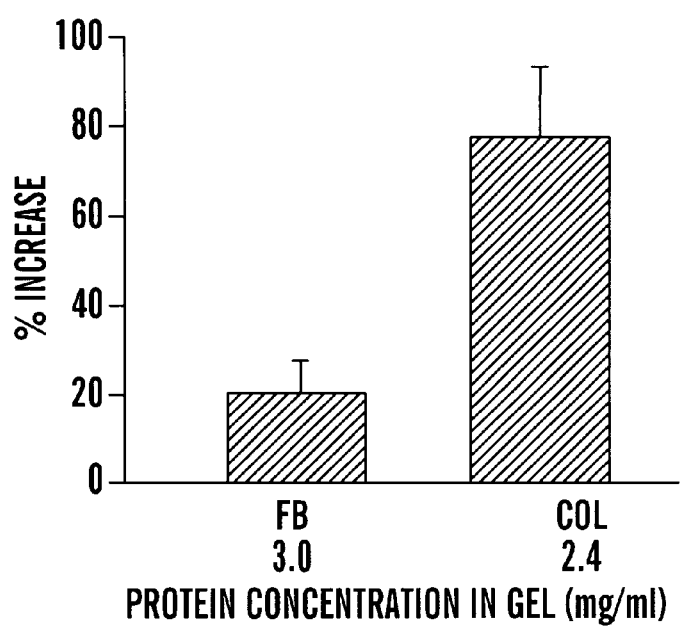

Keratinocyte Outgrowth into Fibrin or Collagen Gels: It remained possible that keratinocytes could migrate as an epidermal sheet more effectively than as single cells, a phenomenon that would not be observed in the phagokinetic assay. When biopsies of human foreskin were placed onto 3-dimensional protein matrices, a modest 20% outgrowth was observed on gels made from highly pure fibrinogen compared to a robust 78% outgrowth on type I collagen gels (FIG. 8B). The outgrowth on collagen gels was, in fact, statistically greater than on fibrin gels ($p<0.0001$ by the Student's T test).

EXAMPLE IX
Keratinocytes Transduced with β3 Integrin Subunit cDNA Adhere to Fibrin(ogen)

Figure 9A:
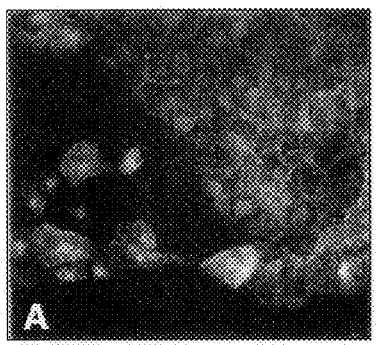
FIGS. 9A–9D illustrate immunofluorescence staining and FACS analysis for αvβ3 integrin receptor on keratinocytes transduced with β3 cDNA (FIGS. 9A and 9C) and β-galactosidase cDNA (FIGS. 9B and 9D). 4th passage transduced keratinocytes were cultured in KGM for 5 days on LAB-TEK tissue culture chamber, fixed with 2% paraformaldehyde for 10 min, and stained with monoclonal antibody to αvβ3 (23C6), biotinylated anti-mouse IgG and fluorescein streptavidin. Cell nuclei were counterstained with 0.1% para-phenylenediamine mounting buffer (Welch et al. 1990). FACS analyses were also performed on 4th passage transduced keratinocytes cultured in KGM. The cell surface expression of αvβ3 was analyzed by flow cytometry performed with a FACStar Plus cell sorter (Becton Dickinson Immunocytometry Systems, San Jose, Calif.)
Figure 9B:
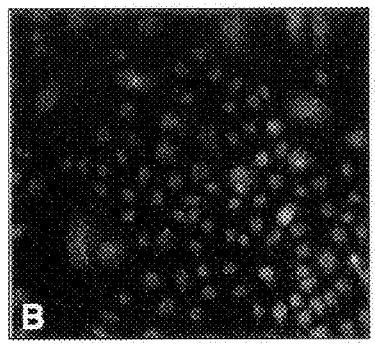
Figure 9C:
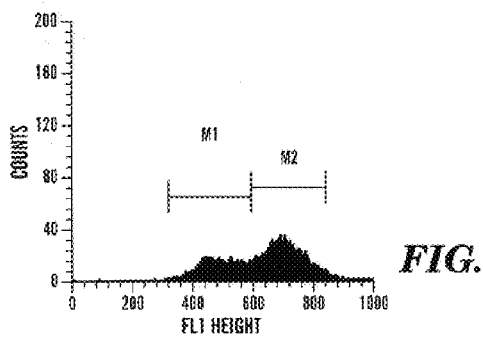
Figure 9D:
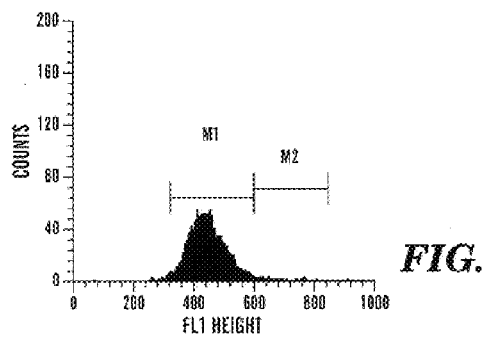
Figure 10:
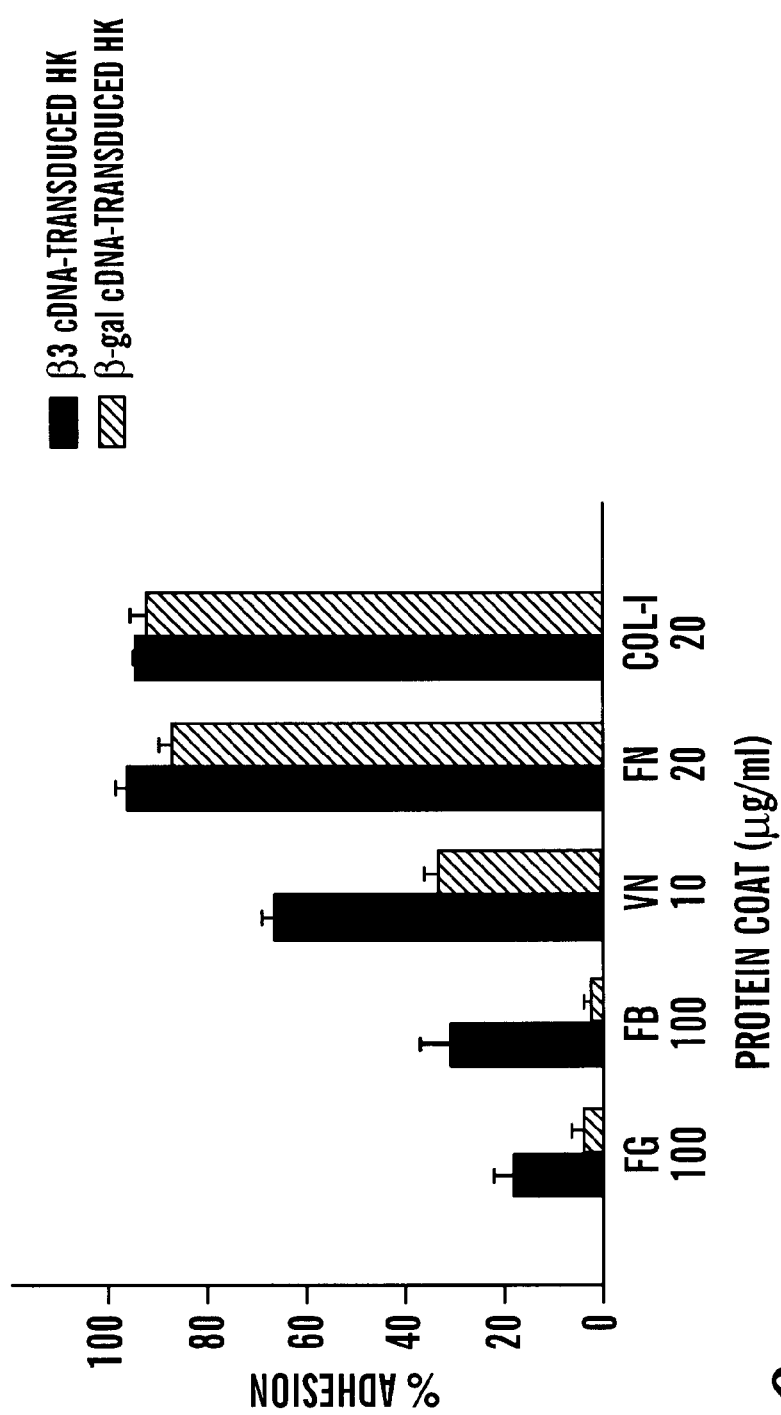
FIG. 10 illustrates cell adhesion of β3 integrin subunit cDNA-transduced and β-galactosidase cDNA-transduced keratinocytes (control) to fibrin(ogen), vitronectin, fibronectin and type I collagen. Cell adhesion assay was done by Method 1. $1 \times 10^4$ viable cells were added to the wells coated with 100 μg/ml FG (coated at 37° C. overnight), 100 μg/ml FB, 10 μg/ml VN, 20 μg/ml FN, 20 μg/ml type I collagen (COL-1). % adhesion was calculated from the net OD value (total OD minus BSA control) of experimental conditions divided by the net OD value of maximal adhesion on poly-L-lysine (total OD minus BSA control). Data points are the mean±standard deviation of quadruplicate samples. The results presented here are representative of 3 independent experiments. Adhesion of β3-transduced keratinocytes to FG, FB, VN and FN was significantly greater than the adhesion of β-gal-transduced keratinocytes to these surfaces as judged by the two-tail Student's T test (p<0.001 for FG, FB and VN; p<0.01 for FN)

Cell surface expression of αvβ3 was detected with the β3 cDNA-transduced keratinocytes by the avidin-biotin immunofluorescence technique (FIG. 9A), while β-gal cDNA-transduced keratinocytes (control) were negative for αvβ3 (FIG. 9B). This was confirmed by FACS analysis (FIGS. 9C and 9D). Two populations of β3-transduced cells were observed on FACS analysis, one positive and one negative for αvβ3 (FIG. 9C). This was in concert with positive and negative populations observed in cultured cells with immunofluorescence technique. Typically cells at the periphery of a colony were positive and those at the center of a colony were negative (data not shown).

β3 cDNA-transduced normal human keratinocytes attached to and spread on fibrinogen and fibrin compared with the control β-gal cDNA-transduced keratinocytes (FIGS. 10 and 11A–11J, respectively). β3 cDNA-transduced keratnocytes also attached to vitronectin significantly better than the control cells (FIG. 10) and spread substantially more (FIGS. 11A–11J). A slight increase of cell attachment and spreading to fibronectin was also observed with the β3 cDNA-transduced keratinocytes compared with control cells (FIGS. 10 and 11A–11J).

Figure 12A:
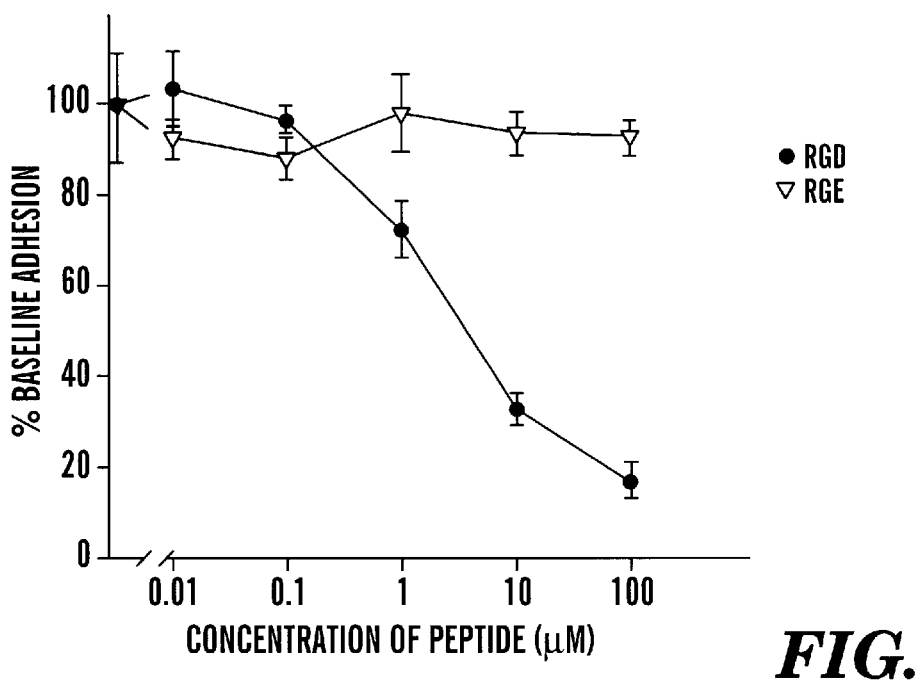
FIGS. 12A and 12B illustrate the inhibition assay by peptides (FIG. 12A) and LM609 (monoclonal antibody to αvβ3) (FIG. 12B) for β3 integrin subunit cDNA-transduced keratinocyte adhesion to FB. 4th passage β3 cDNA-transduced keratinocytes were incubated with various concentrations of LM609, anti-α5β1 monoclonal antibody, anti-human FN polyclonal antibody, or with normal mouse IgG1 (control) for 30 min at 25° C. $1 \times 10^4$ of cells were added to the wells coated with 100 μg/ml FB and were incubated for 1 h at 37° C. Data are expressed as % baseline adhesion of the keratinocytes which were incubated for 30 min without antibody. Data points are the mean±standard deviation of quadruplicate samples. The results presented here are representative of 3 independent experiments.
Figure 12B:
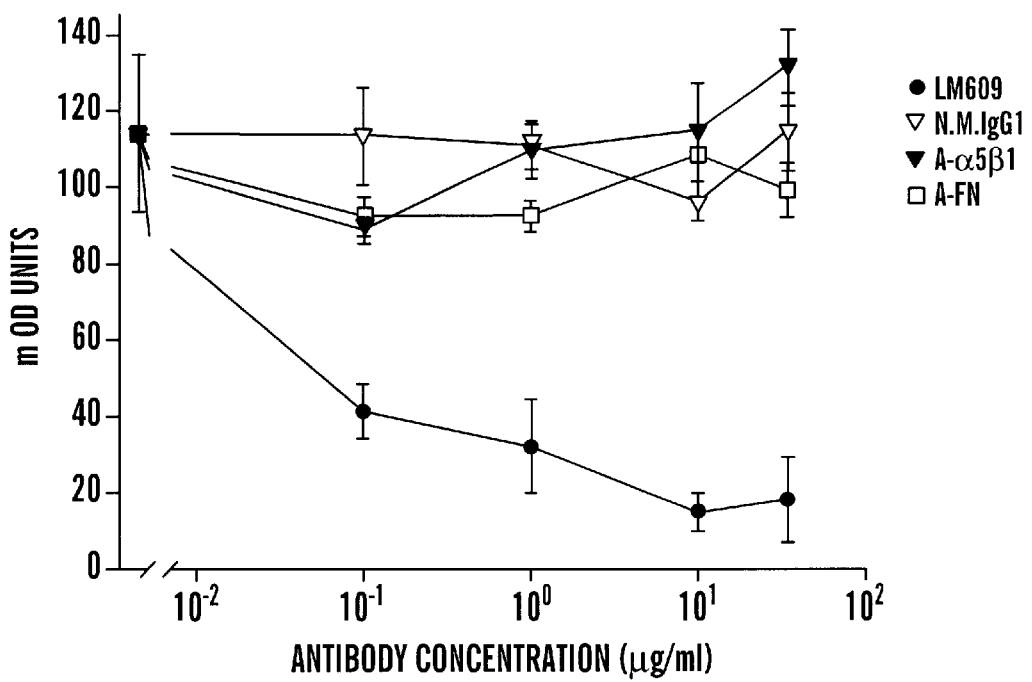

The adhesion of β3-transduced keratinocytes to fibrin was inhibited by RGD peptides (FIG. 12A) and LM609 monoclonal antibody to αvβ3 (FIG. 12B) in a dose-dependent fashion, but not by RGE peptides (FIG. 12A) nor monoclonal antibody to α5, nonimmune mouse IgG, or antibody to human fibronectin (Cappel) (FIG. 12B). These results indicate that the attachment of β3-transduced keratinocytes to fibrin was specific for one of three RGD binding sites in fibrin (Cheresh et al. 1989) and mediated through the αvβ3 integrin receptor (Cheresh and Spiro 1987).

EXAMPLE X

When the basement membrane is destroyed by cutaneous injury, epidermal cells from the wounded edges of the epidermis leave the basement membrane, composed of type IV collagen, laminin and heparan sulfate proteoglycan, and migrate over provisional matrix proteins including type V collagen, fibronectin, tenascin and vitronectin that coat the type I collagen bundles along the cut surface of the wound margin (Clark 1996) In doing so, migrating keratinocytes avoid the fibrin clot (FIGS. 1A–1F), eventually dissecting the fibrin eschar from the wound. Thus the eschar is sloughed rather than incorporated into the wound space. It has recently been demonstrated that the fibrinolytic system is necessary for the migrating epidermis to cleave this fibrin-laden pathway (Romer et al. 1996; Buge et al. 1996). In addition, matrix metalloproteinases are also probably important for keratinocyte penetration under the fibrin clot (Saarialho-Kere et al. 1993; Saarialho-Kere et al. 1994). Nevertheless, how the keratinocytes find the migration pathway is a fundamental, unanswered question.

Tissue cells often use integrin cell surface receptors for adhesion and migration on ECM molecules (Lauffenburger and Horwitz 1996). Although the αvβ3 integrin was originally characterized as a receptor for the plasma protein vitronectin (Hynes 1992), it was later found to bind fibrinogen as well as other provisional matrix proteins (Cheresh 1987). While the platelet and megakaryocyte αIIbβ3 integrin binds fibrinogen and fibrin (Shattil et al. 1994), αvβ3 is the only integrin of tissue cells known to bind these proteins (Chen et al. 1995). Thus the in vivo observation that keratinocytes avoid the fibrin clot coupled with the absence of αvβ3 on keratinocytes in vitro (Adams and Watt 1991) and in vivo (Gailit et al. 1994) predict that keratinocytes may not bind fibrinogen or fibrin. But the interaction of keratinocytes with fibrin or fibrinogen has not yet been conclusively defined as exemplified by a recent paper that demonstrated apparent binding when keratinocytes are allowed to sit on the protein-coated surfaces for up to 30 hours (Weiss et al. 1998), a sufficient time for keratinocytes to remove or alter the protein coat.

Figure 1D:
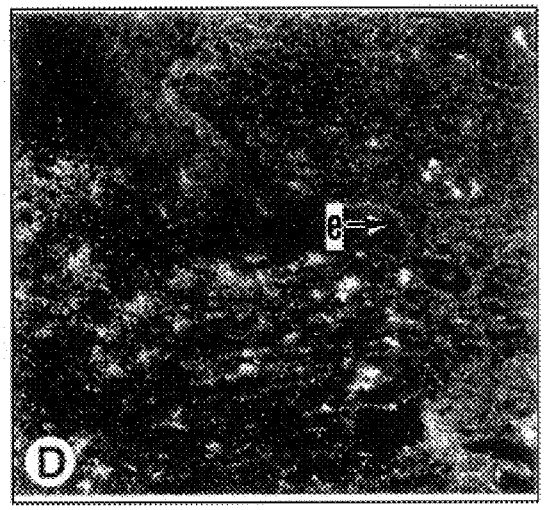
Figure 1E:
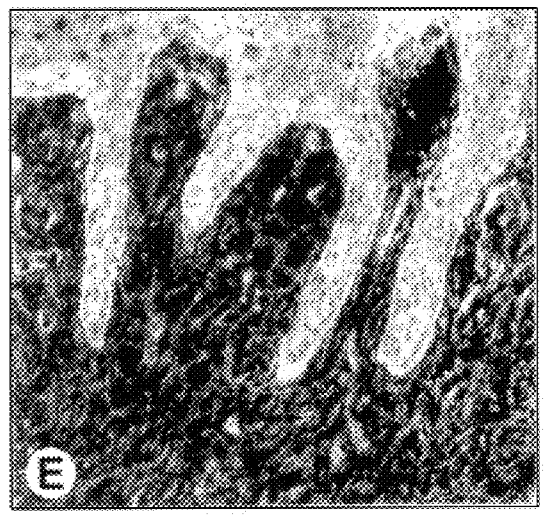
Figure 1F:
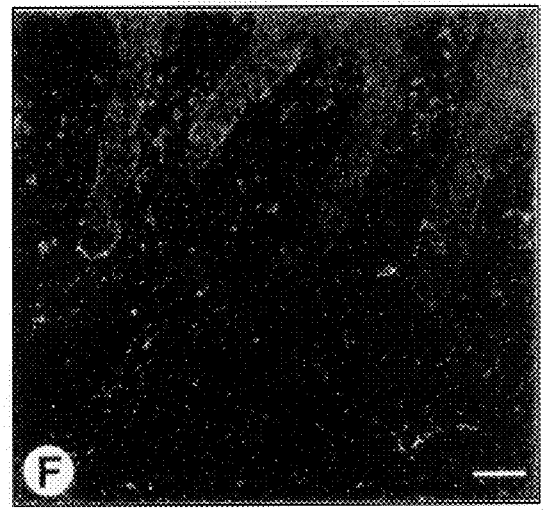
Figure 2A:
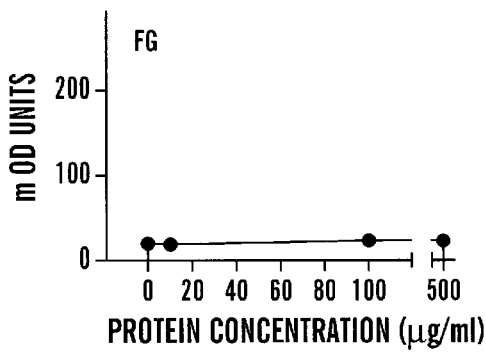
FIGS. 2A–2H illustrate protein dose response curves of human keratinocyte adhesion to fibrinogen, its fragments and other ECM proteins. Cell adhesion assay was by Method 1. Keratinocyte adhesion was measured with protein coat concentrations up to 500 $\mu$g/ml of fibrinogen (FG)(FIG. 2A), FGI-9 (FIG. 2B), and up to 100 $\mu$g/ml of fibrinogen fragments D1 (FIG. 2C) and E1 (FIG. 2D), type I collagen (COL-I) (FIG. 2E), fibronectin (FN) (FIG. 2G), type IV collagen (COL-IV) (FIG. 2F), and laminin (LN) (FIG. 2H). 1×10$^4$ cells were added to each well, and incubated for 1 hr at 37° C. Data points are the mean±standard deviation of quadruplicate samples. The results presented here are representative of 3 independent experiments.
Figure 2B:
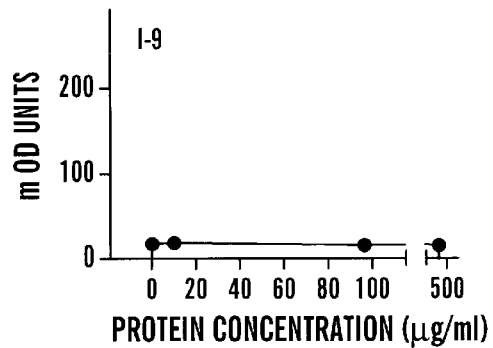
Figure 2C:
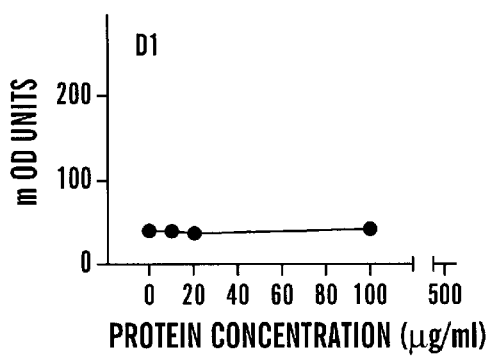
Figure 2D:
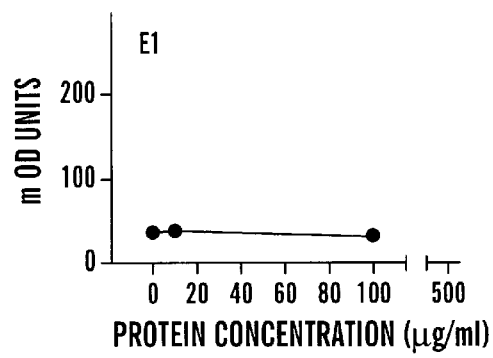
Figure 2E:
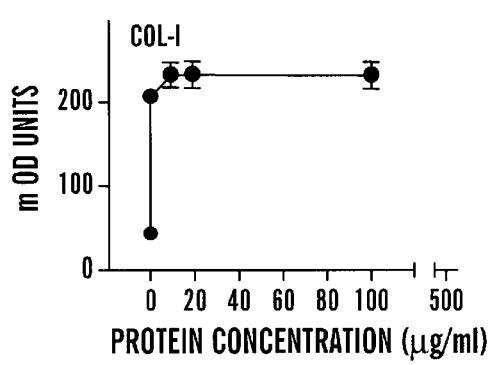
Figure 2F:
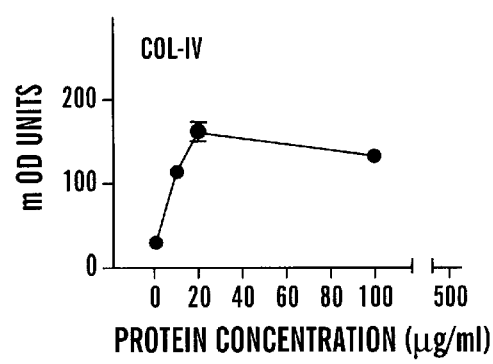
Figure 2G:
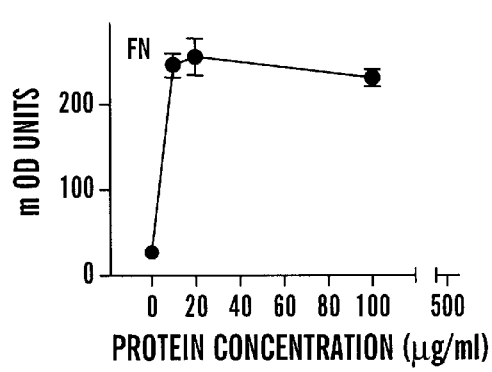
Figure 2H:
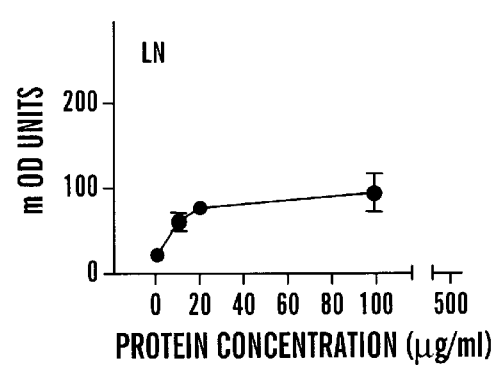

The results herein demonstrate that the migrating wound epidermis does not express αvβ3 (FIG. 1D) but rather expresses αvβ5 (FIG. 1C). The studies reported here were done both with 7G2, a monoclonal antibody to β3, and alternatively with 23C6, a monoclonal to αvβ3. Both monoclonal antibodies gave identical results. Furthermore the capillary tips of blood vessels undergoing angiogenesis in 5 day wounds stained brightly for αvβ3 as previously reported (Clark et al. 1996b) and provided an internal positive control for αvβ3 staining (FIG. 1D).

Cultured human keratinocytes failed to interact with fibrin, fibrinogen or its fragments under any condition tested. Alteration of protein concentration and cell number (data not shown) could not overcome the keratinocyte lack of affinity for fibrin, fibrinogen or its fragments (FIGS. 2A–2H and 3A–3B). The lack of adhesion was also not attributable to an artifact of the adhesion assay since this finding was confirmed by a second adhesion assay (FIGS. 4A–4B) in which centrifugal force rather than repeated washes was used to separate adherent from nonadherent cells (Calof and Lander 1991). Human bladder carcinoma T24 cells which are known to express αvβ3 (Senger et al. 1994) did adhere to fibrin (FIGS. 4A–4B).

It was confirmed, in fact, that human keratinocytes do not produce β3 mRNA (FIG. 5) or αvβ3 surface receptor (Table 1) (Adams and Watt 1991). In contrast, human umbilical vein cells (Cheresh 1987), human dermal fibroblasts (Gailit and Clark 1996), and human microvascular endothelial cells (Enenstein et al. 1992; Klein et al. 1993; Sepp et al. 1994) express αvβ3 and bind fibrinogen and fibrin (Newman et al. 1996; Gailit and Clark 1996; Cheresh 1987). In parallel studies the same adhesion assay (Method 1) that detected fibroblast (Gailit et al. 1997), and microvascular endothelial cell adhesion (Newman et al. 1996) (FIGS. 3A–3B) to fibrin and fibrinogen, detected no keratinocyte attachment to fibrin or fibrinogen. Thus, the possibility that different assay conditions contributed to the differential findings among these three cell types is extremely unlikely.

Keratinocyte adhesion to fibrin, fibrinogen or its fragments could not be stimulated by TGF-β, EGF, TPA, dibutyryl cyclic $\mu$MP or cation alterations (FIGS. 6A–6D), biologic response modifiers known to induce or activate integrin expression in other situations. For example, TGF-β stimulates αvβ3 expression in fibroblasts (Ignotz et al. 1989) and increases αv expression in keratinocytes (Gailit et al. 1994). The keratinocyte αv subunit, however, pairs with β5 or β6 subunits (Larjava et al. 1993; Gailit et al. 1994; Clark et al. 1996a; Haapasalmi et al. 1996), since no β3 is produced (Adams and Watt 1991; Gailit et al. 1994). TGF-β also increases keratinocyte α5β1 receptor expression (Gailit et al. 1994) and in this study enhanced keratinocyte adhesion to fibronectin 2-fold (data not shown). EGF induces α2β1 on human keratinocytes (Chen et al. 1993) and stimulates both adhesion (FIG. 6B) and migration (Chen et al. 1993) on type I collagen. TPA induces α2 mRNA in fibroblasts (Xu et al. 1996) and increased keratinocyte adhesion to type IV collagen (FIG. 6C), a known ligand for α2β1 (Carter et al. 1990). Finally, $MgCl_2$ enhanced keratinocyte binding to types I and IV collagen (FIG. 6D) consistent with its known ability to activate α2β1 integrin receptors in keratinocytes (Grzesiak and pierschbacher 1995). $MgCl_2$ is also known to activate αvβ3 integrin in endothelial cells (Leavesley et al. 1993). Despite the ability of these biologic response modifiers to induce or activate integrins on diverse cell types including keratinocytes, they did not induce keratinocyte adhesion to fibrinogen or fibrin.

Since fibronectin is a substantial component of the in vivo fibrin clot, the ability of human keratinocytes to interact with composites of fibronectin and fibrin or fibrinogen was also tested. Surprisingly, at physiologic 1:10 molar ratios of fibronectin to fibrin or fibrinogen, keratinocytes were unable to interact with fibronectin (FIG. 7A). Even at a 1:1 molar ratio, adhesion of keratinocytes to the composite was markedly diminished compared to keratinocyte adhesion to the equivalent amount of fibronectin adsorbed alone on the surface. These data were not attributable to fibrin or fibrinogen preventing fibronectin from adsorbing to the plastic surface of wells as judged by both isotopic and enzyme-linked-steptavidin bioton assays (FIGS. 7B and 7C, respectively). Thus, fibrin and fibrinogen are clearly anti-adhesives for keratinocytes in that they prevent interaction of the cells to a substrate for which they have great avidity (Chiquet-Ehrismann 1990).

Ultimately the goal is to understand keratinocyte migration during wound re-epithelialization. As a first step toward this goal investigators have been monitoring single cell migration of keratinocytes over a protein coated surface using a modification of the Albrecht-Buehler phagokinetic assay (Albrecht-Buehler 1977). Such studies have demonstrated that ECM molecules found along the cut dermal surface of a cutaneous wound such as fibronectin, type I collagen or vitronectin promote keratinocyte migration while the basement membrane protein laminin 1 inhibits migration (Woodley 1996). Using this assay fibrinogen-coated surfaces failed to promote keratinocyte migration (FIG. 8A) probably secondary to the absence of αvβ3 on keratinocytes (Table 1).

Outmigration of stratified epidermal cells from a cultured skin explant over hydrated three dimensional ECM simulates re-epithelialization better than single cell movement over a protein-coated surface. The difficulty with this paradigm, however, is that a longer incubation (3 days) is necessary compared to the phagokinetic assay (hours). The extended incubation allows keratinocytes time to synthesize and deposit new ECM proteins in the extracellular environment which they can do in vitro (Kubo et al. 1984; O'Keefe et al. 1984) and in vivo (Grimwood et al. 1988). In fact, when in vitro keratinocyte adhesion assays are extended to 24 hr, a time when newly synthesized fibronectin and other newly synthesized proteins can be found in the pericellular matrix (Clark et al. 1985b), there is no discernible difference in keratinocyte adhesion to surfaces coated with fibronectin, fibrinogen, fibrin, types I and IV collagen or laminin (data not shown). Despite this potential complication, keratinocyte outgrowth over a fibrin gel was modest compared to migration over a type I collagen gel (FIG. 8B). Indeed, the low level migration observed on fibrin gels is likely due in part to the presence of fibronectin, newly synthesized by keratinocytes and dermal fibroblasts during the assay. In fact, the finding that stratified epidermal outgrowth moves poorly over a fibrin gel compared to a collagen gel is in concert with in vivo observations that the wound epidermis prefers to migrate along the collagen surface of the cut dermis rather than over or through the fibrin clot.

Thus, human keratinocytes fail to attach and migrate on fibrinogen or fibrin probably through their lack of αvβ3 integrin receptor, which other cells use to interact with fibrinogen and fibrin. Indeed, this possibility was established by the observation that transduction of β3 cDNA into normal human keratinocytes conferred on them the ability to attach and spread on fibrin(ogen) (FIGS. 10 and 11A–11J). β3 cDNA-transduced keratinocytes also attached to and spread on vitronectin significantly more than the control cells. The attachment of β3-transduced keratinocytes to fibrin was inhibited by RGD, but not RGE peptides (FIG. 12A). Fibrin has three RGD-like peptides, RGDF, RGDS and QAGDV (Cheresh et al. 1989). RGDF and RGDS reside on the fibrin α chain, while QAGDV resides on the γ chain. RGDS mediates human umbilical vein endothelial cell binding to fibrin(ogen) through αvβ3, QAGDV mediates platelet binding to fibrin(ogen) through αIIbβ3, while RGDF has no known function (Cheresh et al. 1989). LM609, a monoclonal antibody to αvβ3, blocked β3-transduced keratinocyte adhesion to fibrin, while MoAb#16, a monoclonal blocking antibody of the fibronectin α5β1 integrin receptor (Akiyama et al. 1989), did not block adhesion. From these data it can be concluded that the inability of normal human keratinocytes to interact with fibrin(ogen) is due to their lack of αvβ3 integrin receptor. The absence of this receptor may be one of the fundamental reasons why the migrating epidermis dissects the fibrin clot from viable tissue during wound healing and results in a slough of the fibrin eschar.

Removal of the fibrin clot from the wound also requires plasminogen and either urokinase or tissue plasminogen activator (Romer et al. 1996) and probably interstitial collagenase (MMP-1) (Saarialho-Kere et al. 1993). Successful migration of epidermal cells along a specific route during cutaneous wound repair appears to require an appropriate array of integrins and proteinases working in concert. This is almost certainly a general rule for cell migration through tissue. In at least one situation (angiogenesis), the integrin (αvβ3) and the proteinase (gelatinase A, MMP-2), are intimately linked (Brooks et al. 1996).

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

TABLE 1

Quantitative FACS Analysis of β3 Integrin Subunit and αvβ3 Integrin Expression by Adult Human Keratinocytes and Dermal Fibroblasts

| Monoclonal Antibody | Relative Number of Molecules/Cell (MESF)[a] | |
| --- | --- | --- |
| | Keratinocytes | Fibroblasts |
| 7E3[b] | ns[d] | 13,950 |
| LM609[c] | ns | 14,700 |

[a]MESF values are related to the number of integrin molecules on the cell surface as previously described (Gailit and Clark 1996).
[b]Monoclonal antibody 7E3 reacts with β3 integrin subunit.
[c]Monoclonal antibody LM609 reacts with αvβ3.
[d]Not significant MESF values (<500).

REFERENCES

Abraham, J. A., and M. Klagsbrun. 1996. In: The Molecular and Cellular Biology of Wound Repair. 2nd edition. R. A. F. Clark, editor. Plenum Press, N.Y.

Adams, J. C., and F. M. Watt. 1991. J Cell Biol. 115:829–841.

Akiyama, S. K., et al. 1989. J Cell Biol. 109:863–875.

Albrecht-Buehler, G. 1977. Cell. 11:395–404.

Bergstrom, N., et al. 1994. Treatment of Pressure Ulcers. U.S. Department of Health and Human Services, Clinical Practice Guideline, Vol. 15, Rockville, Md.

Boyce, S. T., et al. 1995. Ann Surg 222:743–752.

Brooks, P. C. et al. 1994. Cell. 79:1157–1164.

Brooks, P.C. et al. 1996. Cell. 85(5):683–693.

Brown, G. L., et al. 1989. N Eng J Med 321:76–79.
Bugge, T. H. et al. 1996. Cell. 87:709–719.
Callam, M. J., et al. 1987. Br med J 294:1389–1391.
Calof, A. L. and A. D. Lander. 1991. J Cell Biol. 115:779–794.
Carter, W. G. et al. 1990. J Cell Biol. 110:1387–1404.
Cavani, A. et al. 1993. J Invest Dermatol. 101:600–604.
Charo, I. F. et al. 1987. J Bio Chem. 262:9935–9938.
Chen, J. D. et al. 1993. Exp Cell Res. 209:216–223.
Chen, Y. -P. et al. 1995. Blood. 86(7):2606–2615.
Cheresh. D. A. 1987. Proc-Natl Acad Sci USA. 84:6471–6475.
Cheresh, D. A. 1991. Cancer Metastasis Rev. 10(1):3–10.
Cheresh, D. A., and R.C. Spiro. 1987. J. Biol Chem. 262:17703–17711.
Cheresh, D. A. et al. 1989. Cell 58:945–953.
Chiquet-Ehrismann, R. 1990. FASEB J. 4:2598–2604.
Chomczynski, P., and N. Sacchi. 1987. Anal Biochem. 162:156–159.
Clark, R. A. F. 1990. J Invest Dermatol. 94 (Suppl):128S–134S.
Clark, R. A. F. 1996. In: The Molecular and Cellular Biology of Wound Repair. 2d edition. R. A. F. Clark, editor. Plenum Press, New York. pp 3–50.
Clark, R. A. F. et al. 1985a. J Invest Dermatol. 84:378–383.
Clark, R. A. F. et al. 1985b. J Cell Biochem. 28:127–141.
Clark, R. A. F. et al. 1996a. Br J Dermatol. 135:46–51.
Clark, R. A. F. et al. 1996b. Am J Path. 148:1407–1421.
Coller, B. S. 1985. J Clin Invest. 76:101–108.
Danen, E. H. et al. 1996. Biochem Biophys Res Commun. 226(1):75–81.
Enenstein, J. et al. 1992. Exp Cell Res. 203:499–503.
Felding-Habermann, B. and D. A. Cheresh. 1993. Curr Opin Cell Biol. 5(5):864–868.
Fitzgerald, L. A. et al. 1987. J Biol Chem. 262:3936–3939.
Folkvord, J. M. et al. 1989. J Histochem Cytochem 37;105–113.
Freed, E. et al. 1989. EMBO J. 8:2955–2965.
Fujii, K. et al. 1995. Exp Cell Res. 216:261–272.
Gailit, J. and R. A. F. Clark. 1996. J Invest Dermatol. 106:102–108.
Gailit, J. et al. 1993. J Invest Dermatol 100:323–328.
Gailit, J. et al. 1994. J Invest Derm. 103:221–227.
Gailit, J. et al. 1996. J Cell Physiol. 169:281–289.
Gailit, J. et al. 1997. Exp Cell Res. 232:118–126.
Gallico, G. G. et al. 1984. N Engl J Med 311(7):448–451.
Garlick, J. A. et al. 1991. J Invest Dermatol. 97:824–829.
Ghazizadeh, S. et al. 1997. J Virology. 71:9163–9169.
Gresham, H. D. et al. 1989. J Cell Biol 108:1935–1943.
Grimwood, R. E. et al. 1988. J Invest Dermatol. 90:434–440.
Grzesiak, J. J., and M.D. Pierschbacher. 1995. J Invest Dermatol. 104:768–774.
Haapasalmi, K. et al. 1996. J Invest Dermatol. 106:42–48.
Heldin, C. -H., and B. Westermark. 1996. In: The Molecular and Cellular Biology of Wound Repair. 2d edition. R. A. F. Clark, editor. Plenum Press, N.Y. pp 249–274.
Hertle, M. D. et al. 1995. J Invest Dermatol. 104 (2):260–265.
Horton, M. A. 1997. Int J Biochem Cell Biol. 29(5):721–725.
Horton, M. A. et al. 1985. Cancer Res. 45:5663–5669.
Hsu, M. Y. et al. 1998. Am J Pathol. 153(5):1435–1442.
Hynes, R. O. 1992. Cell. 69:11–25.
Ignotz, R. A. et al. 1989. J Biol Chem. 264:389–392.
Iwasaki, T. et al. 1994. J Invest Dermatol. 102 (6):891–897.
Juhasz, I. et al. 1993. Am J Path. 143:1458–1469.
Klein, S. et al. 1993. Mol Biol Cell. 4:973–982.
Kubo, M. et al. 1984. J Invest Dermatol. 82:580–586.
Kubo, M. et al. 1987. J Invest Dermatol. 88:594–560.
Kubota, S. et al. 1992. J. Biol. Chem. 267:4285–4288.
Lange, T. S. et al. 1994. Exp Cell Res. 214:381–388.
Larjava, H. et al. 1993. J Clin Invest. 92:1425–1435.
Lauffenburger, D. A., and A. F. Horwitz. 1996. Cell. 84:359–369.
Leavesley, D. I. et al. 1992. J Cell Biol. 117(5):1101–1107.
Leavesley, D. I. et al. 1993. J Cell Biol. 121:163–170.
Lees, T. A., and D. Lambert. 1992. Br J Surg 79:1032–1034.
Lindholm, C., et al. 1992. Acta Derm Venereol (Stockh) 72:227–230.
Markowitz, D. et al. 1988. Virology. 167:400–406.
Matsuyama, T. et al. 1989. J Exp Med 117;1133–1148.
McClain, S. A. et al. 1996. Am J Path. 149:1257–1270.
Medical Data International, Inc. 1993. Wound Card in the US: Emerging trends, management and new product development.
Meh, D. A. et al. 1993. Thromb Res. 70 (6):437–449.
Miller, A. D. 1992. Curr Topics Microbiol Immunol. 158:3–24.
Morgenstern, J. P. and H. Land. 1990. Nucl Acids Res. 18:3587–3596.
Mosesson, M. W. 1974. Semin Thromb Hemostas. 1:63–84.
Mosesson, M. W. 1992. Sem Hematol. 29:177–188.
Mosesson, M. W. et al. 1973. J Biol Chem. 248:7913–7929.
Mosesson, M. W. et al. 1996. J Clin Invest. 97:2342–2350.
Nanney, L. B., and L.E. King. 1996. In: The Molecular and Cellular Biology of Wound Repair. 2d edition. R. A. F. Clark, editor. Plenum Press, New York. pp 171–194.
Newman, D. et al. 1996. J Invest Dermatol. 106:823a.
Odland, G., and R. Ross. 1968. J Cell Biol. 39:135–151.
O'Keefe, E. J. et al. 1984. J Invest Dermatol. 82:150–155.
Phillips, L. G., et al. 1993. Ann Plast Surg 31:331–334.
Phillips, T. J. 1998. Arch Dermatol 134(3):344–349.
Phillips, T. J., and J.S. Dover. 1991. J Am Acad Dermatol 25:965–987.
Phillips, T. J. et al. 1990. J Am Acad Dermatol 23(2 Pt 1)3:189–198.
Randolph, R. K., and M. Simon. 1993. J Biol Chem. 268:9198–9205.
Rheinwald, J. G., and H. Green. 1975. Cell. 6:331–344.

Roberts, A. B., and M. B. Sporn. 1996. In: The Molecular and Cellular Biology of Wound Repair. 2d edition. R. A. F. Clark, editor. Plenum Press, New York. pp 275–310.

Robson, M. C., et al. 1992a. Ann Surg 216:401–406.

Robson, M. C., et al. 1992b. Ann Plast Surg 29:193–201.

Romer, J. et al. 1996. Nature Med. 2:287–292.

Saarialho-Kere, U. K. et al. 1993. J Clin Invest. 92:2858–2866.

Saarialho-Kere, U. K. et al. 1994. J Clin Invest. 94:79–88.

Senger, D. R. et al. 1994. Mol Biol Cell. 5:565–574.

Sepp, N. T. et al. 1994. J Invest Dermatol. 103:295–299.

Shattil, S. J. et al. 1994. Curr Opin Cell Biol. 6 (5):695–704.

Simon, K. O. et al. 1997. J Biol Chem 272(46) :29380–29389.

Suzuki, S. et al. 1990. Proc Natl Acad Sci 87:5354–5358 (1990).

Tonneson, M. G. et al. 1989. J Clin Invest. 83:637–646.

Van De Water, L. et al. 1981. J Cell Biol. 90:32–39.

Wayner, E. A. et al. 1991. J Cell Biol. 113:919–929.

Weiss, E. et al. 1998. J Cell Physiol. 174:58–65.

Welch, M. P. et al. 1990. J Cell Biol. 110:133–145.

Woodley, D. T. 1996. In: The Molecular and Cellular Biology of Wound Repair. R. A. F. Clark, editor. Plenum Press, N.Y. 339–354.

Wu, Y. -J. et al. 1982. Cell. 31:693–703.

Xu, J., and R. A. F. Clark. 1996. J Cell Biol. 132:239–249.

Xu, J. et al. 1996. J Cell Biol. 134:1301–1311.

Yamada, K. M. et al. 1996. In: The Molecular and Cellular Biology of Wound Repair. R. A. F. Clark, editor. Plenum Press, New York. 311–338.

What is claimed is:

1. A recombinant keratinocyte having a nucleic acid encoding a human β3 integrin subunit, wherein said nucleic acid is introduced into said keratinocyte in vitro.

* * * * *